(12) United States Patent
Wilson et al.

(10) Patent No.: US 10,758,335 B2
(45) Date of Patent: Sep. 1, 2020

(54) SYSTEMS AND METHODS FOR ENDOLUMINAL VALVE CREATION

(71) Applicant: InterVene, Inc., South San Francisco, CA (US)

(72) Inventors: Fletcher T. Wilson, San Francisco, CA (US); Douglas Sutton, Pacifica, CA (US); Christopher Scott Jones, Menlo Park, CA (US); Benjamin K. Cline, Palo Alto, CA (US); Mariel Fabro, San Francisco, CA (US)

(73) Assignee: InterVene, Inc., South San Francisco, CA (US)

( * ) Notice: Subject to any disclaimer, the term of this patent is extended or adjusted under 35 U.S.C. 154(b) by 0 days.

(21) Appl. No.: 16/383,504

(22) Filed: Apr. 12, 2019

(65) Prior Publication Data

US 2019/0298510 A1  Oct. 3, 2019

Related U.S. Application Data

(62) Division of application No. 14/377,492, filed as application No. PCT/US2013/025196 on Feb. 7, 2013, now Pat. No. 10,292,807.

(Continued)

(51) Int. Cl.
*A61F 2/06* (2013.01)
*A61B 17/34* (2006.01)
(Continued)

(52) U.S. Cl.
CPC .............. *A61F 2/06* (2013.01); *A61B 1/3137* (2013.01); *A61B 17/00234* (2013.01);
(Continued)

(58) Field of Classification Search
CPC ............ A61B 17/320016; A61B 17/34; A61B 17/3417; A61B 17/3478;
(Continued)

(56) References Cited

U.S. PATENT DOCUMENTS 3,704,711 A  12/1972 Park
4,898,574 A   2/1990 Uchiyama et al.
(Continued)

FOREIGN PATENT DOCUMENTS

CA  1281381 C   3/1991
CA  2678971 A1  8/2008
(Continued)

OTHER PUBLICATIONS

Corcos, I., "A new autologous venous valve by intimal flap: One cases report." Note Di Tecnica, Minerva Cardioangiol, 2003, 51, 10 pages.

(Continued)

*Primary Examiner* — Robert A Lynch
(74) *Attorney, Agent, or Firm* — Perkins Coie LLP

(57) ABSTRACT

Medical systems, devices and methods for creation of autologous tissue valves within a mammalian body are disclosed. One example of a device for creating a valve flap from a vessel wall includes an elongate tubular structure having a proximal portion and a distal portion and a longitudinal axis; a first lumen having a first exit port located on the distal portion of the elongate tubular structure; a second lumen having a second exit port located on the distal portion of the elongate tubular structure; a recessed distal surface on the distal portion of the elongate tubular structure, wherein the recessed distal surface is located distally to the first exit port; and an open trough on the recessed distal surface extending longitudinally from the first exit port.

17 Claims, 41 Drawing Sheets

Related U.S. Application Data

(60) Provisional application No. 61/665,295, filed on Jun. 27, 2012, provisional application No. 61/596,190, filed on Feb. 7, 2012.

(51) Int. Cl.

| | | |
|---|---|---|
| *A61B 1/313* | (2006.01) | |
| *A61B 17/00* | (2006.01) | |
| *A61B 17/06* | (2006.01) | |
| *A61B 17/08* | (2006.01) | |
| *A61F 2/24* | (2006.01) | |
| *A61B 17/3203* | (2006.01) | |
| *A61B 90/00* | (2016.01) | |
| *A61B 1/12* | (2006.01) | |
| *A61B 17/22* | (2006.01) | |
| *A61B 17/32* | (2006.01) | |

(52) U.S. Cl.
CPC ...... *A61B 17/06166* (2013.01); *A61B 17/083* (2013.01); *A61B 17/3417* (2013.01); *A61B 17/3478* (2013.01); *A61F 2/062* (2013.01); *A61F 2/2415* (2013.01); *A61F 2/2475* (2013.01); *A61B 1/126* (2013.01); *A61B 17/32037* (2013.01); *A61B 17/3403* (2013.01); *A61B 2017/0034* (2013.01); *A61B 2017/00557* (2013.01); *A61B 2017/00783* (2013.01); *A61B 2017/00867* (2013.01); *A61B 2017/22071* (2013.01); *A61B 2017/320048* (2013.01); *A61B 2017/346* (2013.01); *A61B 2017/3413* (2013.01); *A61B 2017/3456* (2013.01); *A61B 2090/3784* (2016.02); *A61B 2090/3945* (2016.02); *A61B 2217/007* (2013.01)

(58) Field of Classification Search
CPC ....... A61B 2017/320044; A61B 2017/320048; A61B 2017/320056; A61B 2017/3454; A61B 2017/3456; A61B 2017/346; A61F 2/062; A61F 2/2415; A61F 2/2427; A61F 2/2475

See application file for complete search history.

(56) References Cited

U.S. PATENT DOCUMENTS

| | | | |
|---|---|---|---|
| 4,932,962 | A | 6/1990 | Yoon et al. |
| 5,112,339 | A | 5/1992 | Zelman et al. |
| 5,190,046 | A | 3/1993 | Shturman et al. |
| 5,372,601 | A | 12/1994 | Banning et al. |
| 5,443,443 | A | 8/1995 | Shiber et al. |
| 5,464,395 | A | 11/1995 | Faxon et al. |
| 5,601,588 | A | 2/1997 | Tonomura et al. |
| 5,606,975 | A | 3/1997 | Liang et al. |
| 5,695,507 | A | 12/1997 | Auth |
| 5,738,901 | A | 4/1998 | Wang et al. |
| 5,795,322 | A | 8/1998 | Boudewijn |
| 5,810,847 | A | 9/1998 | Laufer et al. |
| 5,836,945 | A | 11/1998 | Perkins |
| 5,989,276 | A | 11/1999 | Houser et al. |
| 6,190,353 | B1 | 2/2001 | Makower et al. |
| 6,379,319 | B1 | 4/2002 | Garibotto et al. |
| 6,475,226 | B1 | 11/2002 | Farrell et al. |
| 6,506,178 | B1 | 1/2003 | Schubart et al. |
| 6,514,217 | B1 | 2/2003 | Selmon et al. |
| 6,676,665 | B2 | 1/2004 | Foley et al. |
| 6,685,648 | B2 | 2/2004 | Macaulay et al. |
| 6,692,466 | B1 | 2/2004 | Chow et al. |
| 6,702,744 | B2 | 3/2004 | Mandrusov et al. |
| 6,758,836 | B2 | 7/2004 | Zawacki et al. |
| 6,902,576 | B2 | 6/2005 | Drasler et al. |
| 7,008,411 | B1 | 3/2006 | Mandrusov et al. |
| 7,056,325 | B1 | 6/2006 | Makower et al. |
| 7,150,738 | B2 | 12/2006 | Ray et al. |
| 7,179,249 | B2 | 2/2007 | Steward et al. |
| 7,273,469 | B1 | 9/2007 | Chan et al. |
| 7,357,795 | B2 | 4/2008 | Kaji et al. |
| 7,517,352 | B2 | 4/2009 | Evans et al. |
| 7,775,968 | B2 | 8/2010 | Mathis |
| 7,780,592 | B2 | 8/2010 | Tronnes et al. |
| 7,918,870 | B2 | 4/2011 | Kugler et al. |
| 7,927,305 | B2 | 4/2011 | Yribarren et al. |
| 7,938,819 | B2 | 5/2011 | Atkinson et al. |
| 7,955,346 | B2 | 6/2011 | Mauch et al. |
| 8,025,655 | B2 | 9/2011 | Atkinson et al. |
| 8,083,727 | B2 | 12/2011 | Kugler et al. |
| 8,100,860 | B2 | 1/2012 | von Oepen et al. |
| 8,114,123 | B2 | 2/2012 | Brenzel et al. |
| 8,267,947 | B2 | 9/2012 | Ellingwood et al. |
| 8,323,261 | B2 | 12/2012 | Atkinson et al. |
| 8,460,316 | B2 | 6/2013 | Wilson et al. |
| 8,636,712 | B2 | 1/2014 | Atkinson et al. |
| 9,320,504 | B2 | 4/2016 | Wilson et al. |
| 9,545,289 | B2 | 1/2017 | Yu et al. |
| 2001/0041899 | A1 | 11/2001 | Foster |
| 2002/0029052 | A1 | 3/2002 | Evans et al. |
| 2002/0072706 | A1 | 6/2002 | Hiblar et al. |
| 2002/0091362 | A1 | 7/2002 | Maginot et al. |
| 2002/0103459 | A1 | 8/2002 | Sparks et al. |
| 2004/0167558 | A1 | 8/2004 | Igo et al. |
| 2004/0215339 | A1 | 10/2004 | Drasler et al. |
| 2005/0014995 | A1 | 1/2005 | Amundson et al. |
| 2005/0075665 | A1 | 4/2005 | Brenzel et al. |
| 2005/0165466 | A1 | 7/2005 | Morris et al. |
| 2005/0273159 | A1 | 12/2005 | Opie et al. |
| 2006/0094929 | A1* | 5/2006 | Tronnes ............ A61B 17/3478 600/104 |
| 2006/0136045 | A1 | 6/2006 | Flagle et al. |
| 2006/0178646 | A1 | 8/2006 | Harris et al. |
| 2006/0184187 | A1 | 8/2006 | Surti |
| 2006/0235449 | A1 | 10/2006 | Schubart et al. |
| 2006/0271090 | A1 | 11/2006 | Shaked et al. |
| 2007/0005093 | A1 | 1/2007 | Cox et al. |
| 2007/0093780 | A1 | 4/2007 | Kugler et al. |
| 2007/0093781 | A1 | 4/2007 | Kugler et al. |
| 2007/0208368 | A1 | 9/2007 | Katoh et al. |
| 2008/0033467 | A1 | 2/2008 | Miyamoto et al. |
| 2008/0103480 | A1 | 5/2008 | Bosel et al. |
| 2008/0228171 | A1 | 9/2008 | Kugler et al. |
| 2008/0243065 | A1 | 10/2008 | Rottenberg et al. |
| 2009/0005793 | A1 | 1/2009 | Pantages et al. |
| 2009/0112059 | A1 | 4/2009 | Nobis et al. |
| 2009/0182192 | A1 | 7/2009 | Shiono et al. |
| 2009/0209910 | A1 | 8/2009 | Kugler et al. |
| 2009/0254051 | A1 | 10/2009 | von Oepen et al. |
| 2010/0076476 | A1 | 3/2010 | To et al. |
| 2010/0152682 | A1 | 6/2010 | Mauch et al. |
| 2010/0152843 | A1 | 6/2010 | Mauch et al. |
| 2010/0256599 | A1 | 10/2010 | Kassab et al. |
| 2011/0264125 | A1* | 10/2011 | Wilson ................ A61B 90/02 606/159 |
| 2011/0264127 | A1 | 10/2011 | Mauch et al. |
| 2011/0264128 | A1 | 10/2011 | Mauch et al. |
| 2012/0143234 | A1 | 6/2012 | Wilson et al. |
| 2012/0289987 | A1 | 11/2012 | Wilson et al. |
| 2013/0066346 | A1 | 3/2013 | Pigott et al. |
| 2013/0103070 | A1 | 4/2013 | Kugler et al. |
| 2013/0116715 | A1 | 5/2013 | Weber |
| 2013/0216114 | A1 | 8/2013 | Courtney et al. |
| 2013/0317534 | A1 | 11/2013 | Zhou et al. |
| 2014/0012301 | A1 | 1/2014 | Wilson et al. |
| 2015/0057566 | A1 | 2/2015 | Vetter et al. |
| 2015/0094532 | A1 | 4/2015 | Wilson et al. |
| 2015/0265263 | A1 | 9/2015 | Wilson et al. |
| 2015/0342631 | A1 | 12/2015 | Wilson et al. |
| 2015/0359630 | A1 | 12/2015 | Wilson et al. |
| 2016/0166243 | A1 | 6/2016 | Wilson et al. |
| 2016/0235428 | A1 | 8/2016 | Wilson et al. |
| 2017/0035450 | A1 | 2/2017 | Wilson et al. |
| 2017/0035455 | A1 | 2/2017 | Wilson et al. |
| 2018/0000509 | A1 | 1/2018 | Wilson et al. |

(56) References Cited

U.S. PATENT DOCUMENTS

| | | |
|---|---|---|
| 2018/0214173 A1 | 8/2018 | Wilson et al. |
| 2018/0289441 A1 | 10/2018 | Wilson et al. |
| 2018/0333166 A1 | 11/2018 | Wilson et al. |

FOREIGN PATENT DOCUMENTS

| | | |
|---|---|---|
| CN | 1907243 A | 2/2007 |
| CN | 1957861 A | 5/2007 |
| JP | 2002514111 A | 5/2002 |
| JP | 2003033357 A | 2/2003 |
| JP | 2003267160 A | 9/2003 |
| JP | 2009165822 A | 7/2009 |
| JP | 2009183516 A | 8/2009 |
| RU | 2108751 C1 | 4/1998 |
| RU | 2160057 C2 | 12/2000 |
| WO | 99000059 A1 | 1/1999 |
| WO | 2008/063621 A2 | 5/2008 |
| WO | 2010074853 A1 | 7/2010 |
| WO | 2011106735 A1 | 9/2011 |
| WO | 2012145444 A2 | 10/2012 |
| WO | 2013119849 A1 | 8/2013 |
| WO | 2014110460 A1 | 7/2014 |

OTHER PUBLICATIONS

International Search Report and Written Opinion for International App. No. PCT/US2013/025196, dated Apr. 25, 2013, 7 pages.

Lugli, et al., Neovalve construction in the deep venous incompetence. J. Vasc. Surg., Jan. 2009, 49(1), 156-62.

Maleti, O., Neovalve construction in postthrombotic syndrome. Journal of Vascular Surgery, vol. 34, No. 4, 6 pages.

Extended European Search Report dated Jul. 6, 2015, for European Patent Application No. 13747210.6, 7 pages.

Foreign Office Action dated Apr. 26, 2018, for European Patent Application No. 13747210.6, 5pages.

* cited by examiner

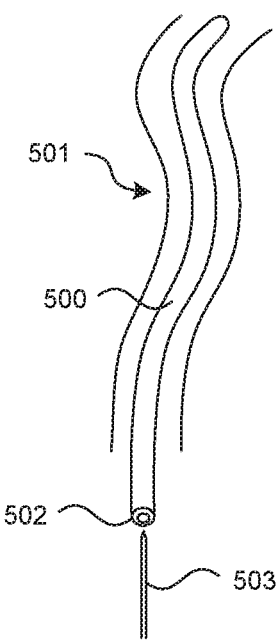
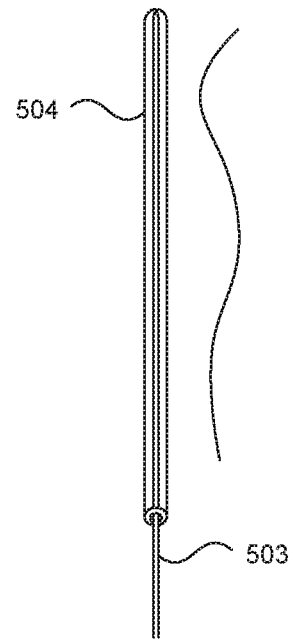
FIG. 5A  FIG. 5B
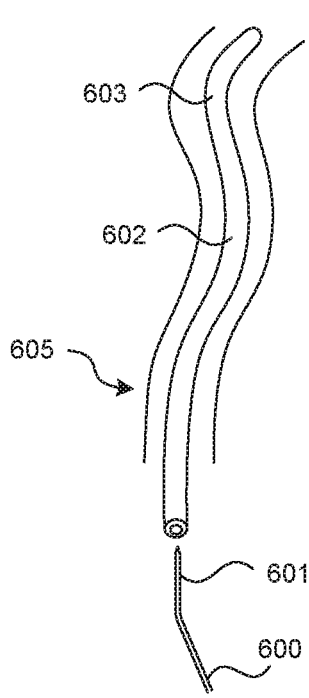
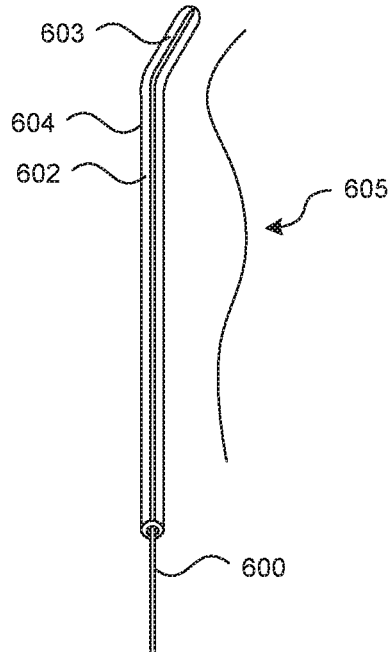
FIG. 6A  FIG. 6B

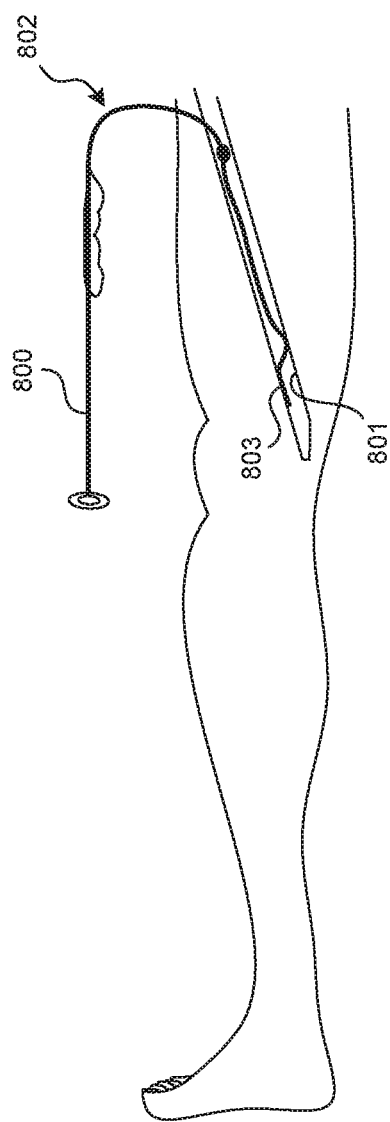
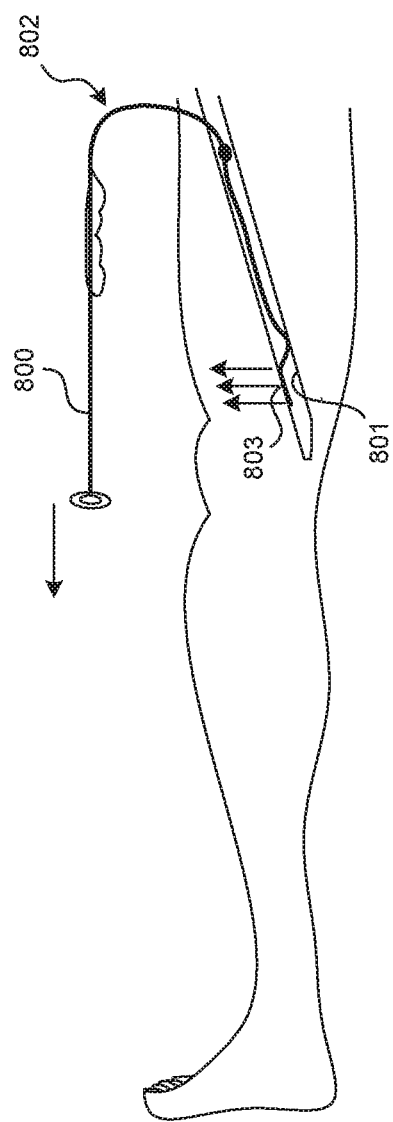
FIG. 8A
FIG. 8B

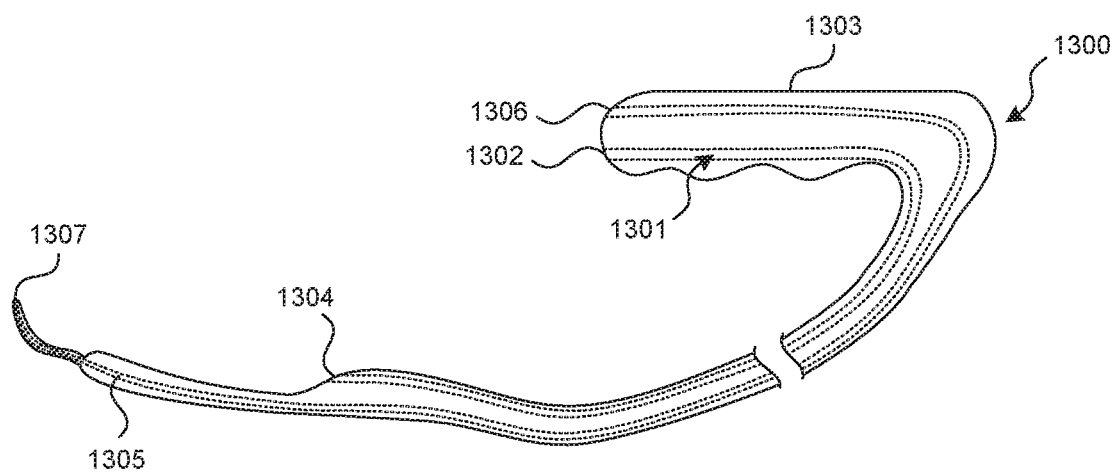
FIG. 13A
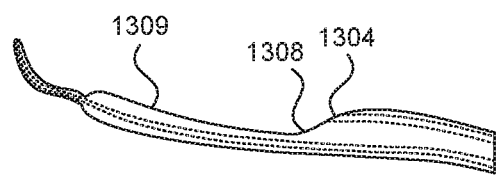
FIG. 13B
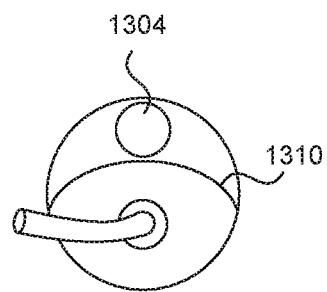 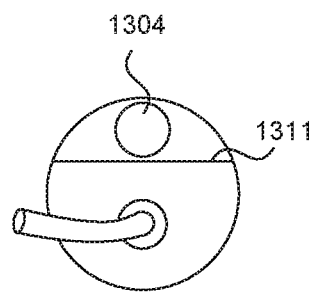
FIG. 13C    FIG. 13D

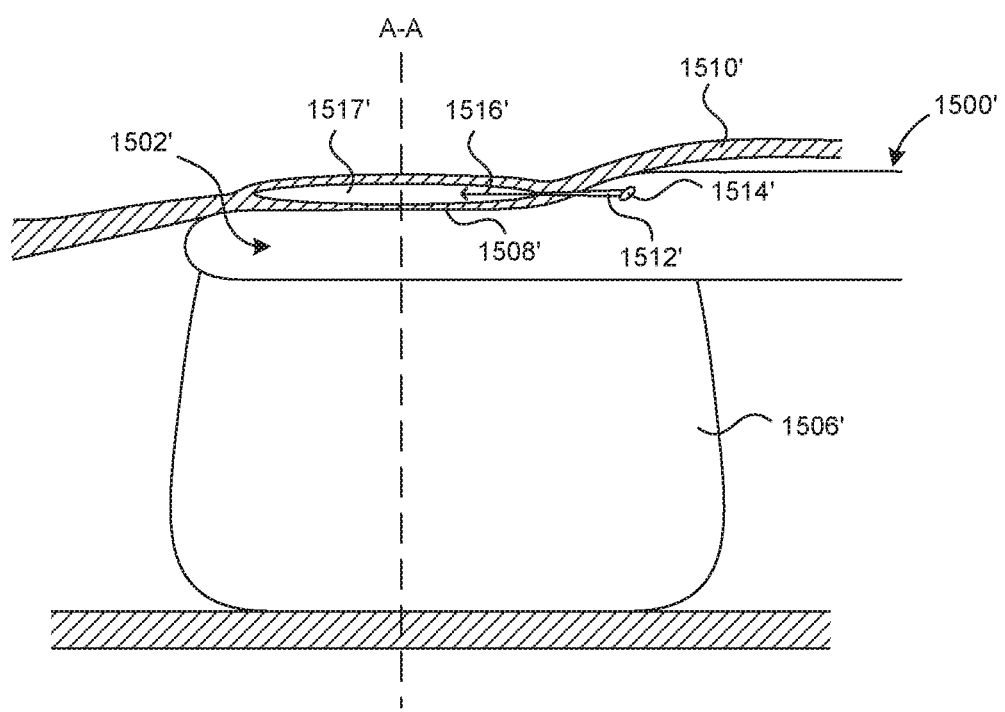
FIG. 15.5A

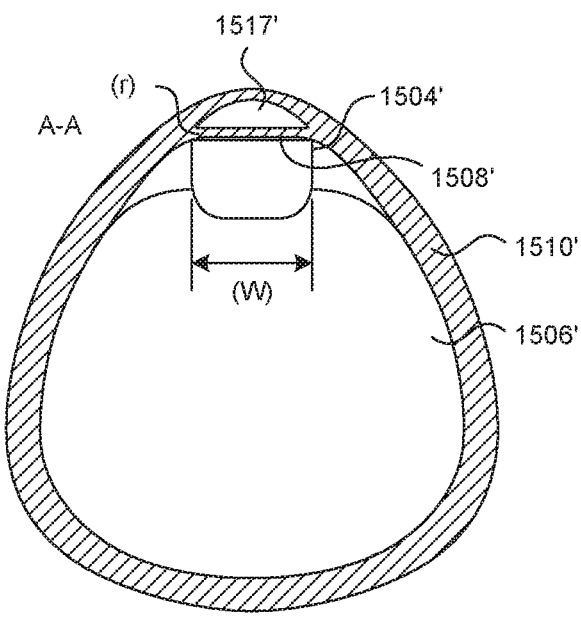
*FIG. 15.5B*
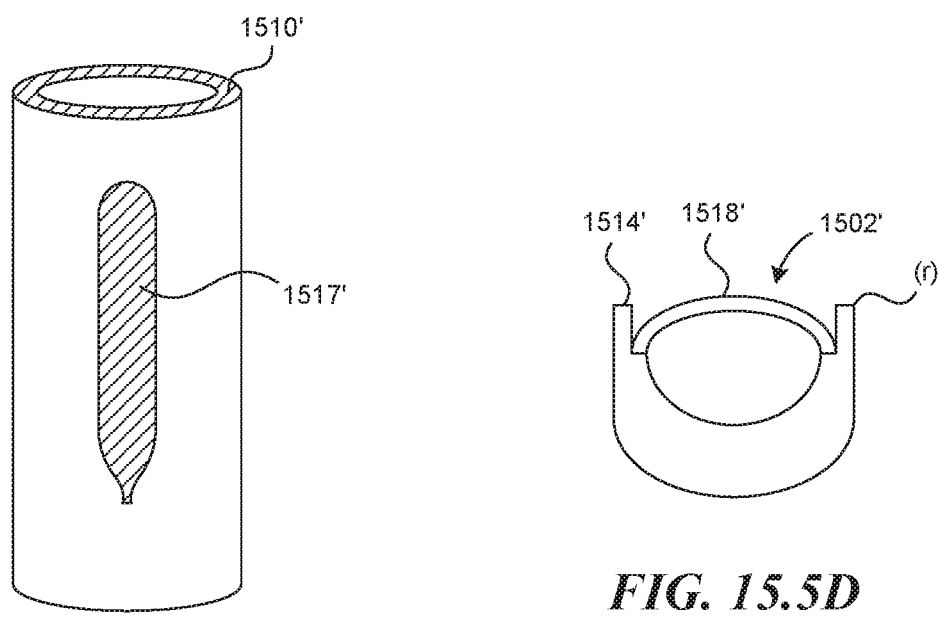
*FIG. 15.5C*
*FIG. 15.5D*

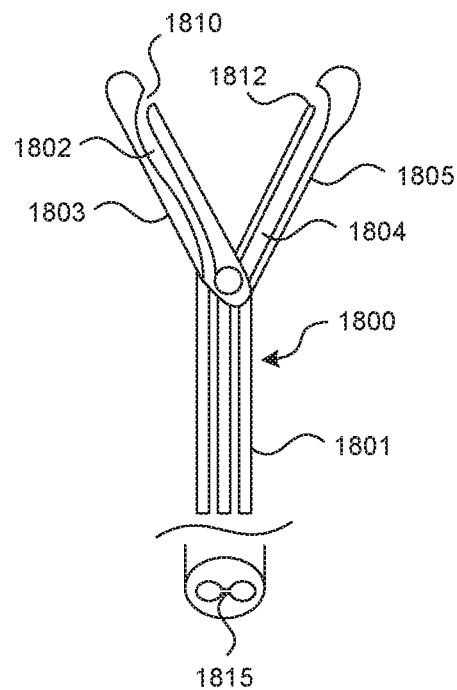
FIG. 18A
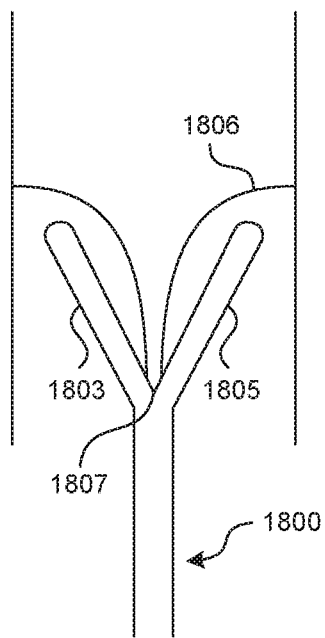 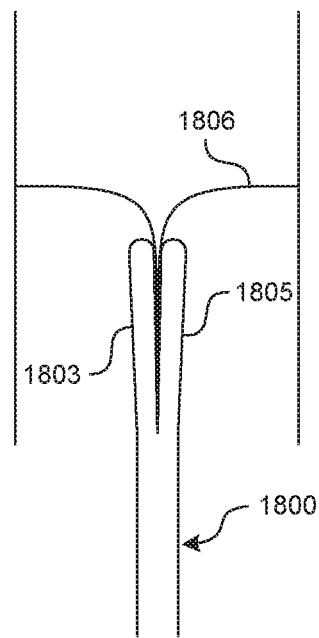
FIG. 18B     FIG. 18C

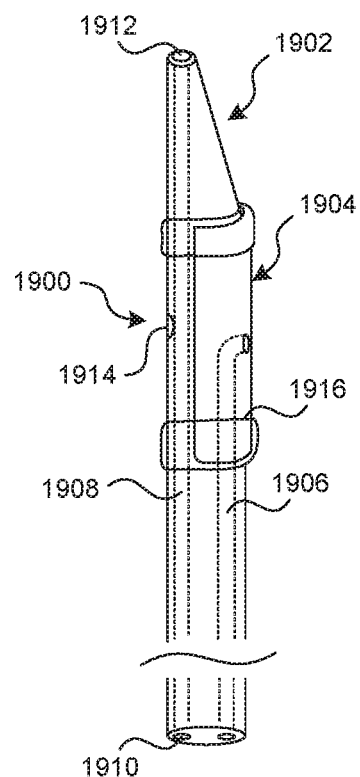 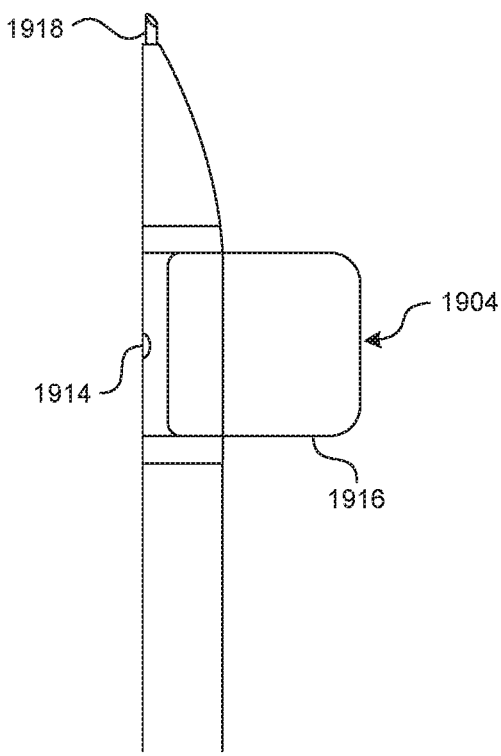
*FIG. 19A*      *FIG. 19B*
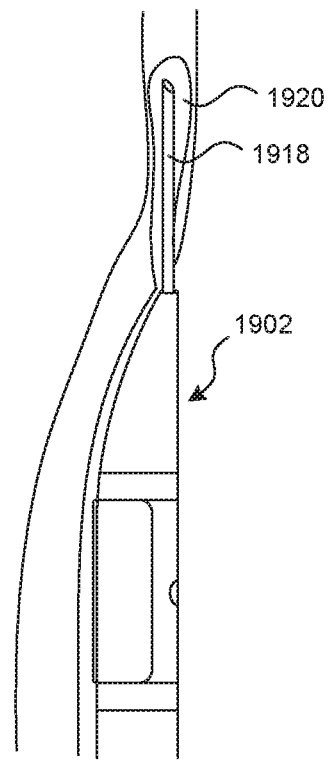 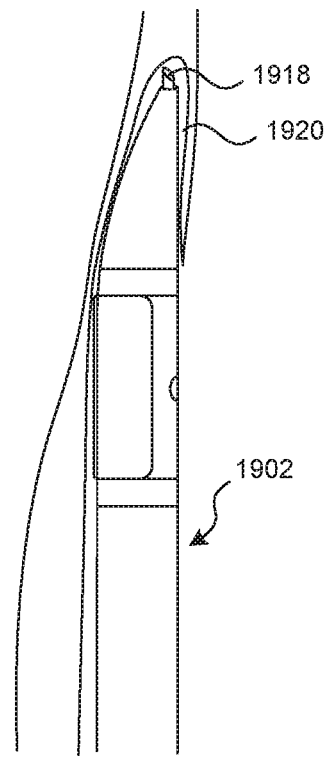
*FIG. 19C*      *FIG. 19D*

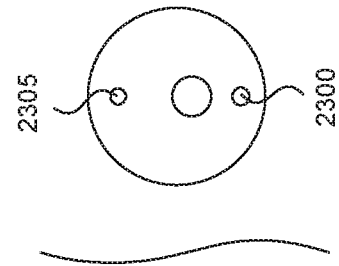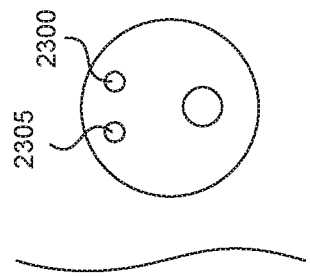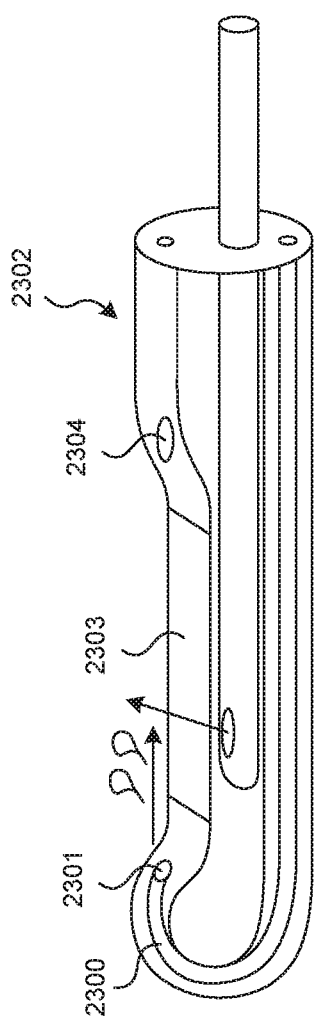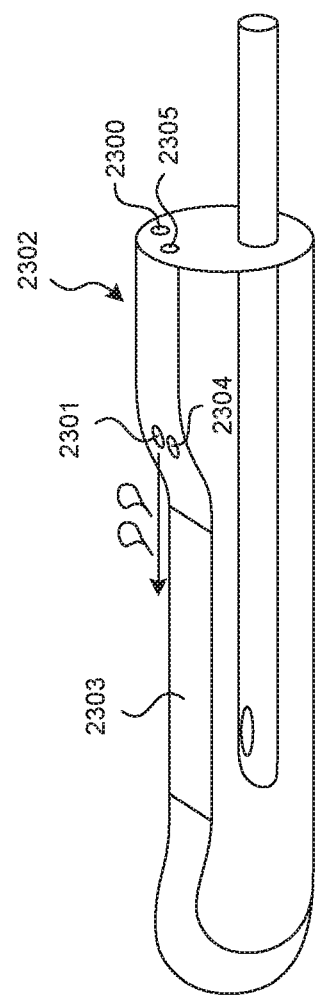
*FIG. 23A*  *FIG. 23B*

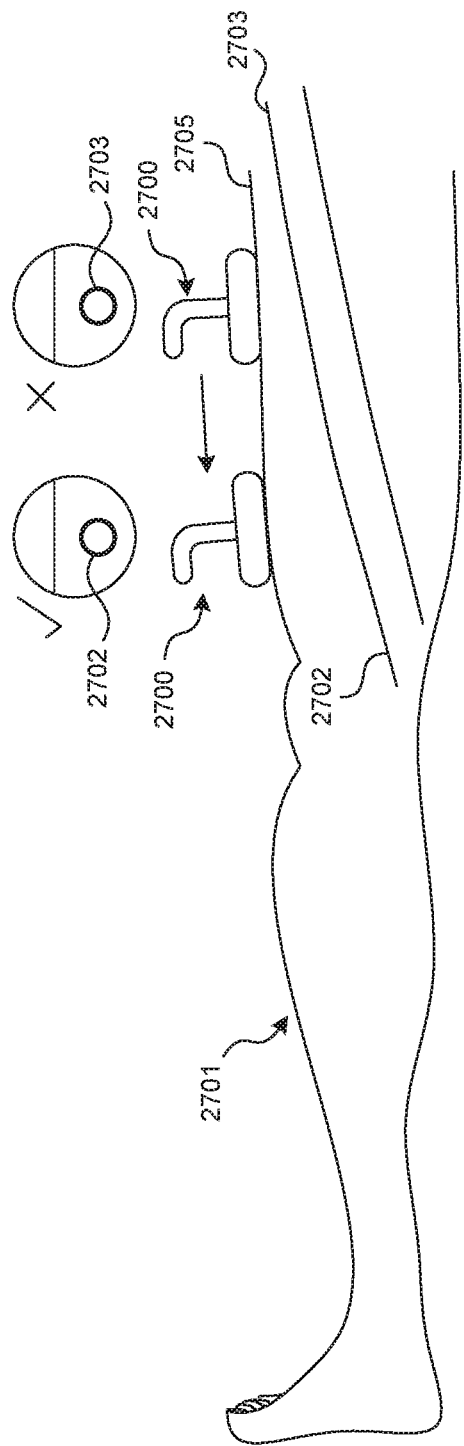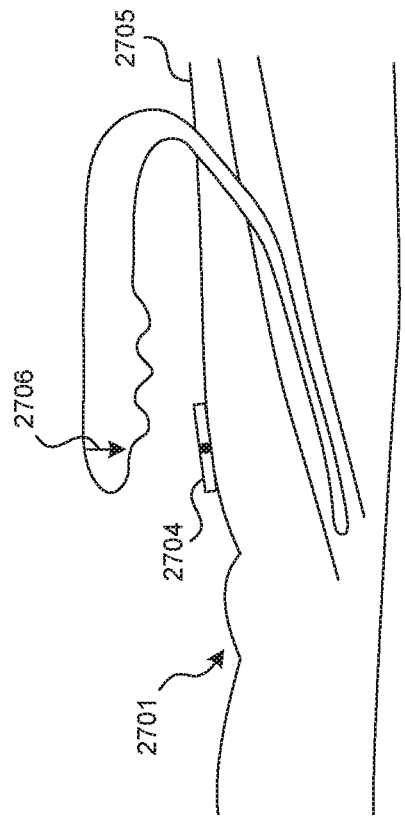
FIG. 27A
FIG. 27B

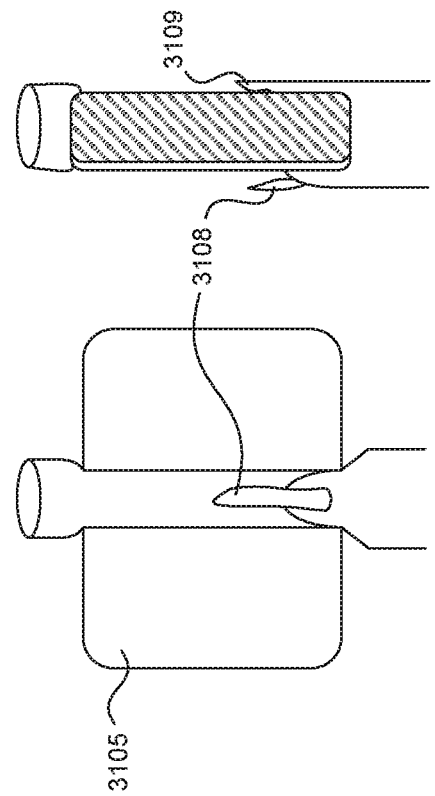
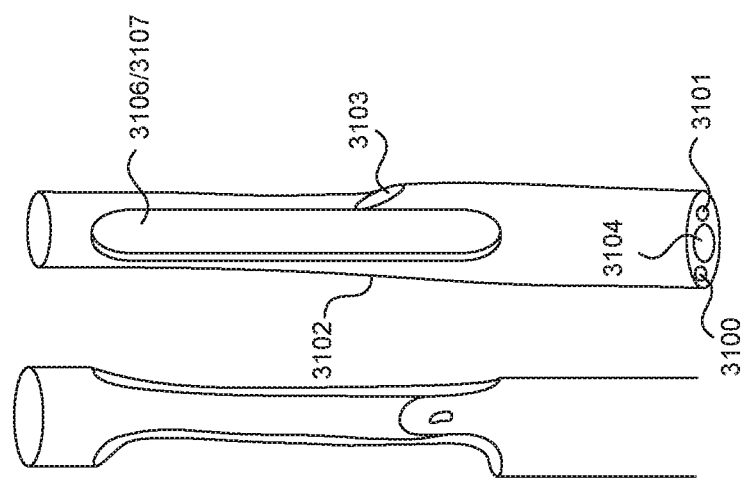
FIG. 31B
FIG. 31A

SYSTEMS AND METHODS FOR ENDOLUMINAL VALVE CREATION

CROSS-REFERENCE TO RELATED APPLICATIONS

This application is a divisional of U.S. patent application Ser. No. 14/377,492, filed Aug. 7, 2014, which is a 35 U.S.C. 371 U.S. National Phase application of International Application No. PCT/US2013/025196, filed Feb. 7, 2013, which claims the benefit of U.S. Provisional Application No. 61/596,190 filed Feb. 7, 2012 and U.S. Provisional Application No. 61/665,295 filed Jun. 27, 2012, which are hereby incorporated by reference in their entireties for all purposes.

INCORPORATION BY REFERENCE

All publications and patent applications mentioned in this specification are herein incorporated by reference to the same extent as if each individual publication or patent application was specifically and individually indicated to be incorporated by reference.

TECHNICAL FIELD

Embodiments of the present invention relate generally to medical systems, devices and methods for creation of autologous tissue valves within a mammalian body.

BACKGROUND

Venous reflux is a medical condition affecting the circulation of blood, such as in the lower extremities or neck. The valves in the vessel that normally force blood back towards the heart cannot function properly. As a result, blood flows backwards, causing unwanted clinical problems such as ulceration or even multiple sclerosis when chronic cerebrospinal venous insufficiency is present. Applicant of the subject application determines that new systems and methods for treating venous reflux would be desirable.

SUMMARY

The present invention relates generally to medical systems, devices and methods for creation of autologous tissue valves within a mammalian body.

In some embodiments, a device for accessing a valve creation site on a vessel wall is provided. The device can include a handle; an elongate tubular structure having a proximal end and a distal end, wherein the proximal end of the elongate tubular structure is attached to the handle, wherein the elongate tubular structure is sized and configured for insertion into a vessel of a patient; and a valve navigation mechanism extending from the distal end of the elongate tubular structure, wherein the valve navigation mechanism has a smaller cross-sectional profile than the elongate tubular structure.

In some embodiments, the handle has a configuration that doubles back towards the distal end of the elongate tubular structure.

In some embodiments, the valve navigation mechanism is thinner and has a smaller diameter than the elongate tubular structure. In some embodiments, the valve navigation mechanism is more flexible than the elongate tubular structure. In some embodiments, the valve navigation mechanism has an elongate body that is curved along its length. In some embodiments, the valve navigation mechanism has an atraumatic tip.

In some embodiments, the device further includes a tool lumen extending through the elongate tubular structure, the tool lumen having an exit port located on a first side of a distal portion of the elongate tubular structure.

In some embodiments, the device further includes an expansion element aligned with the exit port and located a second side of the distal portion of the elongate tubular structure, wherein the first side is opposite the second side.

In some embodiments, the device further includes a predetermined off-set between the exit port and a recessed distal surface on the distal portion of the elongate tubular structure, wherein the recessed distal surface is located distally to the exit port. In some embodiments, the recessed distal surface is flat. In some embodiments, the off-set is ramped. In some embodiments, the off-set is less than 2 mm.

In some embodiments, the device further includes a puncture element extending out of the exit port, wherein the predetermined offset is configured to control the depth of penetration of the puncture element into the vessel wall, wherein the depth of penetration is less than the thickness of the vessel wall. In some embodiments, the puncture element comprises an expansion mechanism. In some embodiments, the expansion mechanism is a balloon. In some embodiments, the puncture element has an asymmetrical tip.

In some embodiments, a device for creating a valve flap from a vessel wall is provided. The device can include an elongate tubular structure having a proximal portion and a distal portion and a longitudinal axis; a first lumen having a first exit port located on the distal portion of the elongate tubular structure; a recessed distal surface on the distal portion of the elongate tubular structure, wherein the recessed distal surface is located distally to the first exit port; and a visualization window located on the recessed distal surface.

In some embodiments, the device further includes a visualization mechanism that is slidably disposed proximate the visualization window.

In some embodiments, the device further includes a flush port located on the elongate tubular structure proximally to the visualization window, wherein the flush port faces or is tangent to the visualization window.

In some embodiments, the device further includes a flush port located on the elongate tubular structure distally to the visualization window, wherein the flush port faces or is tangent to the visualization window.

In some embodiments, a device for creating a valve flap from a vessel wall is provided. The device can include an elongate tubular structure having a proximal portion and a distal portion and a longitudinal axis; a first lumen having a first exit port located on the distal portion of the elongate tubular structure; a second lumen having a second exit port located on the distal portion of the elongate tubular structure; a recessed distal surface on the distal portion of the elongate tubular structure, wherein the recessed distal surface is located distally to the first exit port; and an open trough on the recessed distal surface extending longitudinally from the first exit port.

In some embodiments, the device further includes a visualization tool slidably disposed in the first lumen, wherein the visualization tool is configured to have a stowed configuration in which the visualization tool is contained in the first lumen and an extended configuration in which the visualization tool extends from the first lumen and into the open trough which is configured to guide the visualization tool.

In some embodiments, the device further includes a puncture element slidably disposed in the second lumen.

In some embodiments, the device further includes a puncture element identifier located on a distal portion of the puncture element, wherein the puncture element identifier is configured to assist in locating the puncture element.

In some embodiments, the puncture element identifier is selected from the group consisting of a reflective surface, a light source and an ultrasound transducer.

In some embodiments, the open trough has a depth that is between ¼ to ¾ of the trough diameter.

In some embodiments, the device further includes a flushing lumen having a flush port proximate the first exit port and the second exit port.

In some embodiments, the flushing lumen has a winged configuration.

In some embodiments, the device further includes an expandable element located on the opposite side of distal portion of the elongate tubular structure than the recessed distal surface. In some embodiments, the device further includes an inflation window located on the opposite side of the distal portion of the elongate tubular structure than the recessed distal surface; a third lumen in communication with the inflation window; and a removable expansion element slidably disposed in the third lumen.

In some embodiments, a device for creating and fixing a valve leaflet from a vessel wall is provided. The device can include an elongate tubular structure having a tapered distal end; an expandable element located on a first side of the elongate tubular structure, the expandable element having a proximal end and a distal end; a sideways facing exit port located on a second side of the elongate tubular structure between the proximal end and the distal end of the expandable element, wherein the second side is opposite the first side, wherein the sideways facing exit port is located a predetermined distance from the proximal end of the expandable element; and a lumen in communication with the sideways facing exit port; wherein the expandable element is configured to create the valve leaflet from the vessel wall when expanded from a collapsed configuration to an expanded configuration such that the sideways facing exit port is pressed against the valve leaflet.

In some embodiments, the expandable element is configured to create the valve leaflet from the vessel wall when expanded from a collapsed configuration to an expanded configuration such that the sideways facing exit port is pressed against the valve leaftlet a predetermined distance from a terminating edge of the valve leaflet.

In some embodiments, the expandable element is configured to create the valve leaflet from the vessel wall when expanded from a collapsed configuration to an expanded configuration such that the valve leaflet is pressed against another anatomical structure.

In some embodiments, the elongate tubular structure has a distal end with a tapered portion.

In some embodiments, the tapered portion is asymmetrical and is located on the first side of the elongate tubular structure.

In some embodiments, the device further includes a puncture element disposed within the lumen, wherein the puncture element contains a valve fixation element.

In some embodiments, the valve fixation element is made of a shape memory material.

In some embodiments, a device for the fixation of two created valve leaflets is provided. The device can include a shaft having a first lumen and a second lumen and a longitudinal axis; a first tong extending from a distal end of the shaft, wherein the first lumen extends within the first tong and terminates in a first inwardly and sideways facing exit port; a second tong extending from the distal end of the shaft, wherein the second lumen extends within the second tong and terminates in a second inwardly and sideways facing exit port; wherein the first tong and the second tong have an opened configuration and a closed configuration, wherein the first port and the second port are aligned within a predetermined distance from each other in the closed configuration.

In some embodiments, the first tong and the second tong are rotatably attached to the distal end of the shaft.

In some embodiments, the device further includes a fastening mechanism disposed within at least one of the first lumen and the second lumen. In some embodiments, the fastening mechanism comprises a deployment structure with a suture or a clip.

In some embodiments, a device for accessing a valve creation site on a vessel wall is provided. The device can include a handle; an elongate tubular structure having a proximal end and a distal end, wherein the proximal end of the elongate tubular structure is attached to the handle, wherein the elongate tubular structure is sized and configured for insertion into a vessel of a patient; a valve navigation mechanism extending from the distal end of the elongate tubular structure, wherein the valve navigation mechanism has a smaller cross-sectional profile than the elongate tubular structure; a tool lumen extending through the elongate tubular structure, the tool lumen having an exit port located on a first side of a distal portion of the elongate tubular structure; a recessed distal surface on the distal portion of the elongate tubular structure, wherein the recessed distal surface is located distally to the exit port; a predetermined off-set between the exit port and the recessed distal surface; and a puncture element disposed within the tool lumen, wherein the predetermined offset is configured to control the depth of penetration of the puncture element into the vessel wall, wherein the depth of penetration is less than the thickness of the vessel wall.

In some embodiments, a method of creating a valve flap from a vessel wall of a vessel is provided. The method can include providing an elongate tubular structure having a proximal portion and a distal portion and a longitudinal axis, a first lumen having a first exit port located on the distal portion of the elongate tubular structure, a recessed distal surface on the distal portion of the elongate tubular structure, wherein the recessed distal surface is located distally to the first exit port, and a visualization mechanism located proximate the first exit port; inserting the elongate tubular structure into the vessel; advancing the elongate tubular structure within the vessel wall; imaging the vessel wall with the visualization mechanism to identify a location on the vessel wall suitable for formation of the valve flap; advancing a puncture element through the first lumen and into the vessel wall to a first depth within the vessel wall without penetrating entirely through the vessel wall; and infusing a hydrodissection fluid into the vessel wall through the puncture element to separate a portion of the vessel wall into two layers and form a hydrodissection pouch.

In some embodiments, the method further includes infusing a fluid into the vessel to dilate the vessel and increase the tension on the vessel wall.

In some embodiments, the puncture element has a beveled tip.

In some embodiments, the method further includes rotating the beveled tip to control the advancement of the puncture element into the vessel wall to the first depth.

In some embodiments, the method further includes pressing the recessed distal surface into the vessel wall to control the formation of the hydrodissection pouch.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 5A-5B illustrate an embodiment of a device having a flexible structure for accessing a valve creation site that can be straightened with a stiffening mechanism.

FIGS. 6A-6B illustrate another embodiment of a device having a flexible structure for accessing a valve creation site that can be straightened with a stiffening mechanism.

FIGS. 8A-8B illustrate another embodiment of a device for accessing a valve creation site that has a pull wire to manipulate the distal end of the device.

FIGS. 13A-13D illustrate an embodiment of a device for accessing a valve creation site that has a tool lumen.

FIGS. 15.5A-15.5D illustrate an embodiment of a device that uses hydrodissection to separate tissue layers.

FIG. 18A-18D illustrate an embodiment of a flap fixation device and method.

FIG. 19A-19I illustrate another embodiment of a flap fixation device that can be used with an embodiment of a valve creation mechanism.

FIGS. 23A-23B illustrate various embodiments of a visualization assisting mechanism involving a flushing lumen.

FIGS. 27A-27D illustrate various embodiments of ultrasound based visualization mechanism.

FIGS. 31A-31B illustrate an embodiment of a bicuspid valve creation device and method.

DETAILED DESCRIPTION

Methods and Devices for Accessing a Valve Creation Site and Gaining Wall Apposition and Tautness In accordance with some embodiments, an apparatus, such as a vessel wall puncture device, is described that upon being advanced to the preferred site within a vessel, manipulates the orientation of a vessel to better perform a vessel wall puncture. All embodiments described for accessing a valve creation site and gaining wall apposition and tautness (covering FIGS. 1-9, and all associated text that may or may not describe embodiments depicted in figures), can be used in combination with other components described for full valve creation, including but not limited to: gaining access into an intra-mural space, use of direct or indirect visualization methods, creation of an intra-mural pocket, valve mouth opening, and valve securement for full valve creation. An example of one way in which to combine embodiments to complete the valve creation procedure is depicted in FIG. 19. The embodiments depicted here can be used in combination with these or similar techniques to create a full valve geometry. Another similar example of one way in which to combine embodiments to complete the valve creation procedure is depicted in FIG. 30. The embodiments depicted here can be used in combination with these or similar techniques to create a full valve geometry.

Figure 1A:
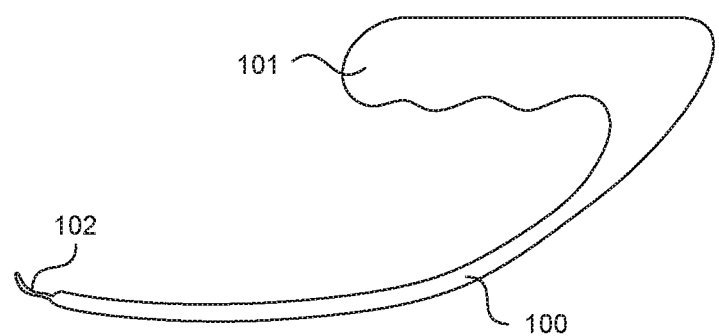
FIGS. 1A-1B illustrate various views of an embodiment of a device for accessing a valve creation site.

In some embodiments of such an apparatus, as is depicted in FIG. 1 (1A side view, 1B for top view), the tubular structure 100 to be inserted into a vessel is substantially rigid, not flexible. This rigid tubular structure is connected on the proximal end to a handle 101, which allows for ease of insertion of the device. In the embodiment depicted, the handle 101 takes an orientation such that it doubles back in the direction of the distal end of the rigid tubular structure 100. This may allow for easier insertion in the high femoral vein in the presence of a large abdominal protuberance that may hinder vessel access. In some embodiments, the rigid tubular structure 100 is connected on the distal end to a valve navigation mechanism 102, which helps the device navigate existing venous valves from above. The valve navigation mechanism 102 can be thinner with a smaller diameter than the rigid tubular structure 100. Additionally, the valve navigation mechanism 102 may be more flexible than the tubular structure. Additionally, the valve navigation mechanism 102 may have a slight curvature to it, so that rotation of the tubular mechanism allows for more lateral movement of the tip of the navigation mechanism, while will assist in finding the opening of a valve. Additionally, the valve navigation mechanism 102 may have an atraumatic rounded tip.

Figure 1B:
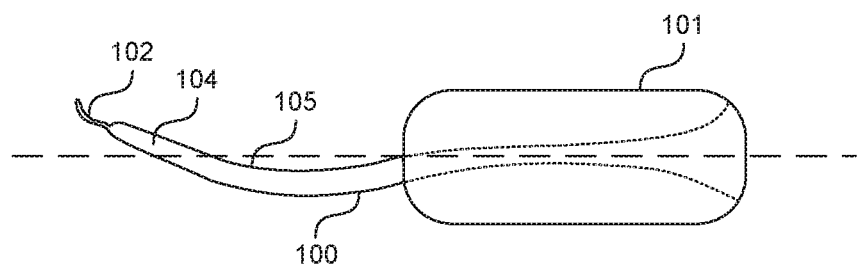

In the embodiment depicted, the apparatus form is catered toward use in the femoral or popliteal vein, to be accessed from above. In addition, the device can be used in the femoral or popliteal veins, to be accessed from below. In addition, the device can be used in other veins and/or other blood vessels and/or other lumens. In one specific aspect of the form depicted, the distal end of the tubular structure 100 curves upward toward the handle 101 and flattens out to a strait section 104 nearly parallel to the axis of the handle 101 shown. The distal end 106 is where much of the tissue manipulation will occur. In some embodiments (as depicted in FIG. 1B), the tubular structure may include a subtle curved portion 105, which is advantageous for navigating through venous valves or other types of vasculature. In some embodiments, the curved portion 105 curves laterally with respect to the longitudinal axis L of the device. In some embodiments, the curvature of the curved portion 105 may have a radius of curvature between 6 inches and 3 ft. In other embodiments, it may have a radius of curvature between 1 ft and 2 ft. In other embodiments, it may have a radius of curvature between 1.25 ft and 1.75 ft.

Figure 2A:
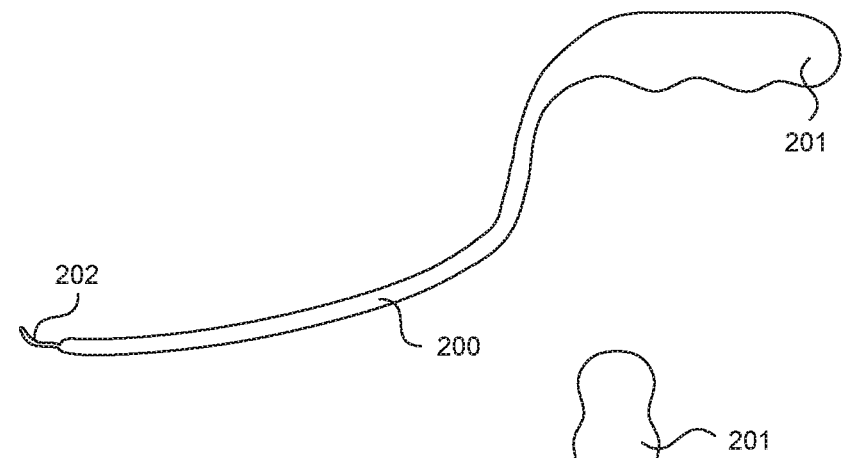
FIGS. 2A-2B illustrate other embodiments of a device for accessing a valve creation site with alternative handle configurations.
Figure 2B:
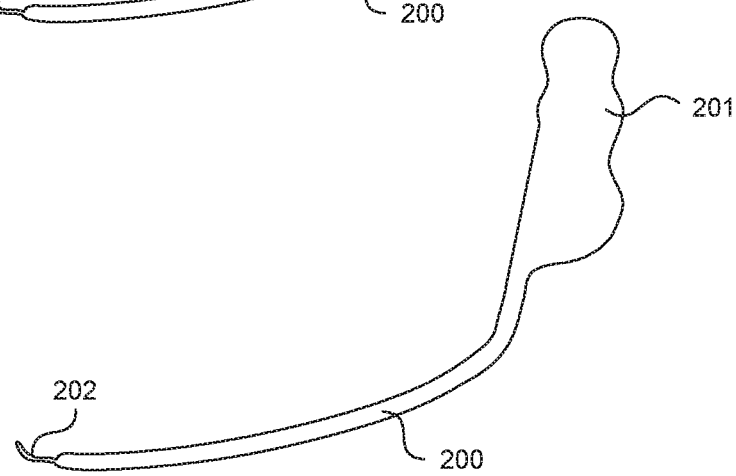

Other embodiments shown in FIG. 2, include alternate handle forms, which provide various advantages for insertion or manipulation. FIG. 2A depicts a rigid tubular structure 200 connected to a handle 201 pointing away from the distal end 202 of the tubular structure. This may be advantageous in inserting the device in a patient with a relatively shallow vessel. It also may allow for a large degree of allowed rotation. It also, maybe allow for a better ergonomic feel for the user. It also may be advantageous for passing rigid devices through the handle to the distal end. FIG. 2B depicts a rigid tubular structure 200 connected to a handle 201 pointing upward at about a 90-degree angle with respect to the shaft of the tubular structure 200. This may be advantageous in inserting the device in an overweight patient with a large abdominal section. Other embodiments can have a handle that is angled between about 0 degrees as shown in FIG. 2A to about 90 degrees as shown in FIG. 2B.

Figure 3A:
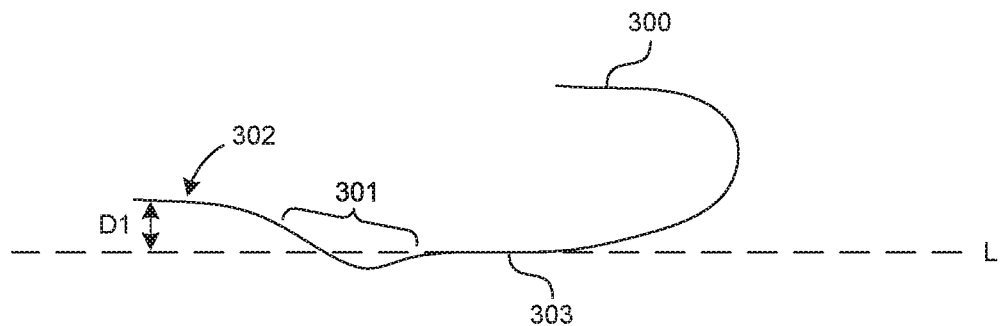
FIGS. 3A-3C illustrate various embodiments of a device for accessing a valve creation site.
Figure 3B:
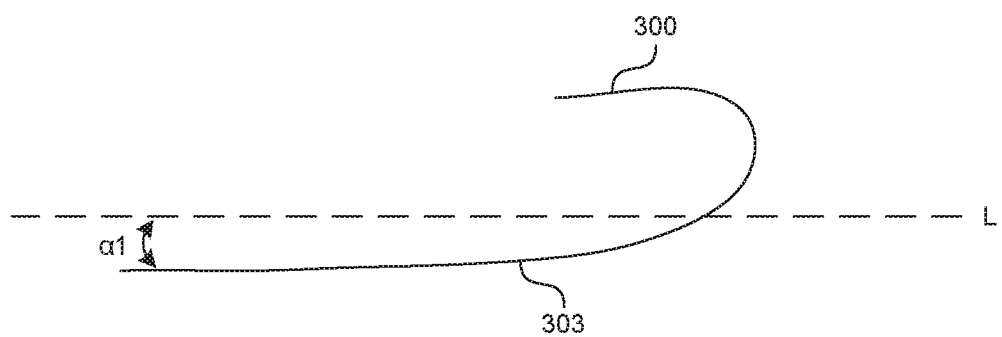
Figure 3C:
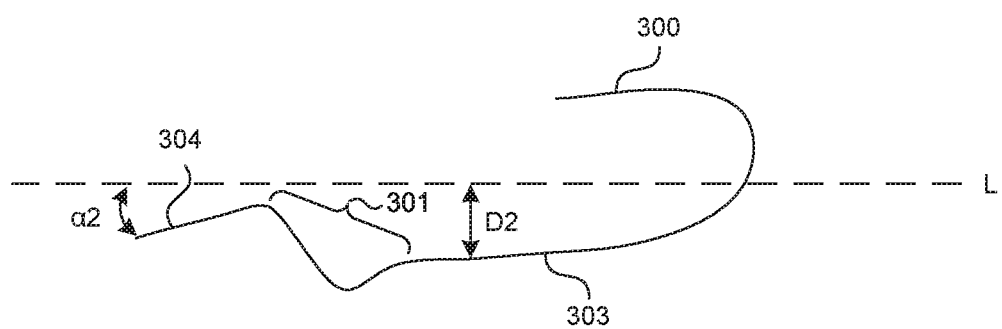
Figure 4A:
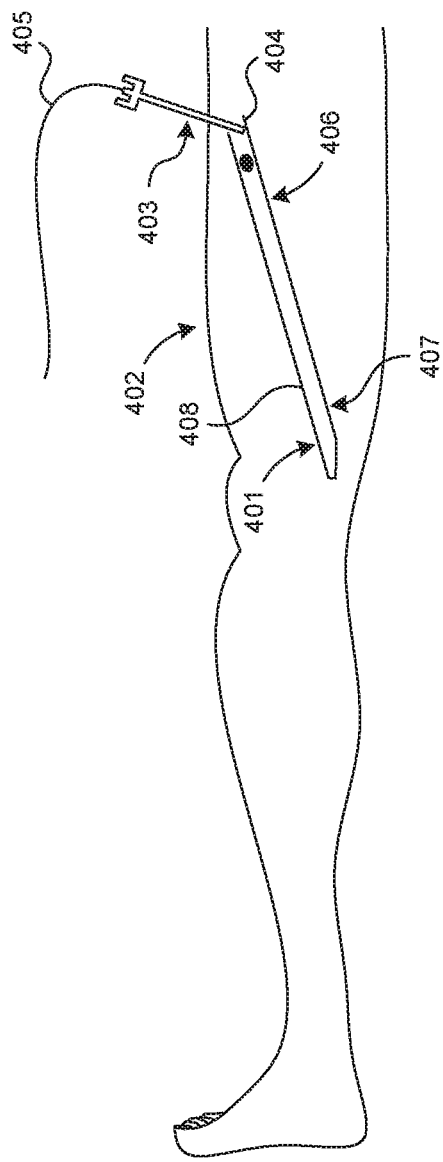
FIGS. 4A-4D illustrate the use of an embodiment of a device for accessing a valve creation site to access the valve creation site and gain wall apposition.
Figure 4B:
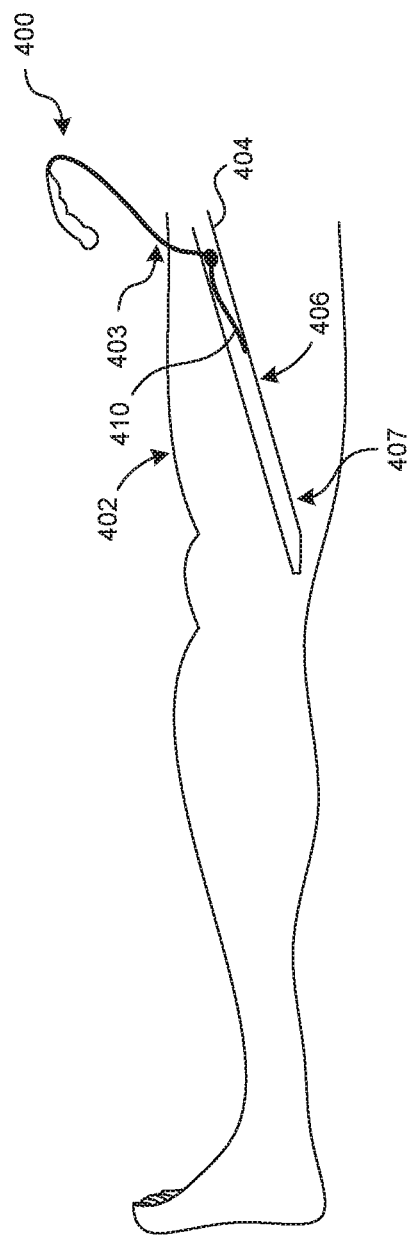
Figure 4C:
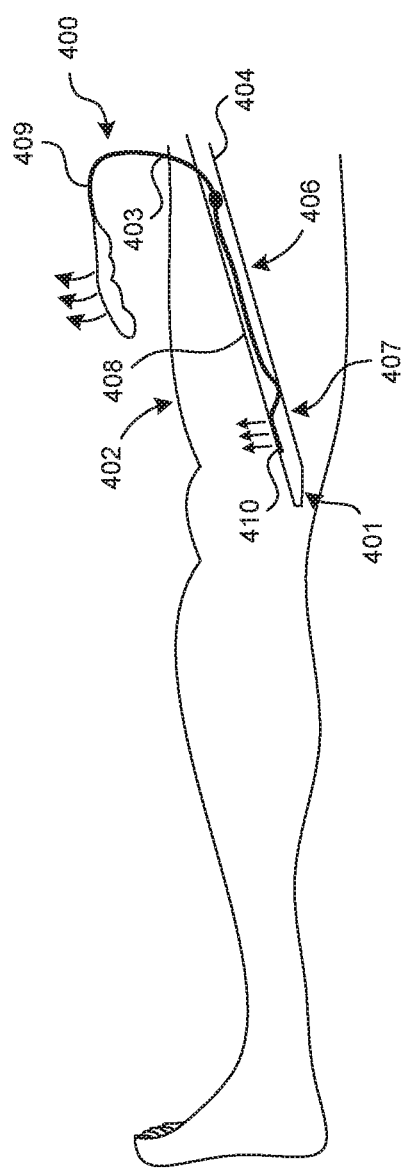
Figure 4D:
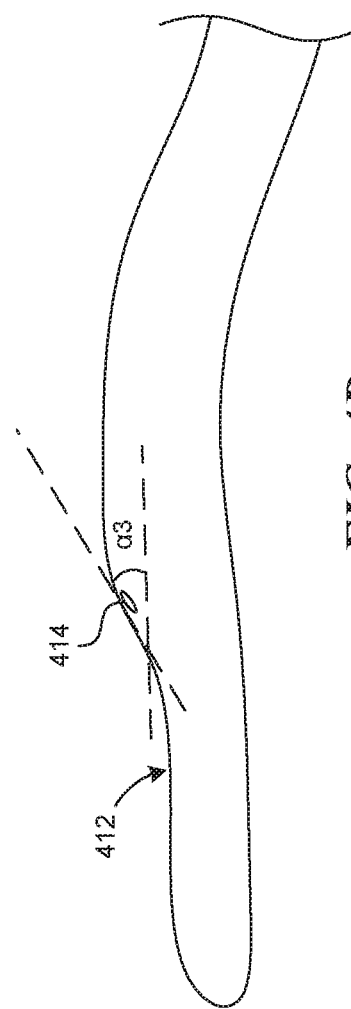

Other embodiments shown in FIG. 3, show side views of different specific shapes the apparatus may take, all oriented with the handle 300 in the horizontal position which corresponds to parallel with the supine leg (not depicted). FIG. 3A shows a tubular structure 303 with a double bend 301 near the distal end, with an elevated horizontal distal platform 302 that can be substantially parallel with the handle and longitudinal axis L. In some embodiments, each bend can have a radius of curvature between 0.5 inch and 2 ft. In other embodiments, each bend can have a radius of curvature between 1 inch and 1 ft. In other embodiments, each bend can have a radius of curvature between 3 inches and 9 inches. The elevation D1 of the elevated horizontal distal platform 302 above the horizontal proximal portion of the tubular structure 303 can be between about 1 mm to 20 mm. In other embodiments, the elevation may be between 3 mm and 10 mm. In other embodiments, the elevation may be between 4 mm and 7 mm. In some embodiments, D1 can be approximately equal to the diameter of the vein or blood vessel where the surgical procedure, such as valve creation, is to be performed. FIG. 3B shows a tubular structure 303 with a constant downward angle α1 with respect to the longitudinal axis L. Angle α can be between about 0 to 30 degrees, or 5 to 20 degrees, or 10 to 18 degrees. FIG. 3C shows a double bend 301 near the distal end, with an elevated but downward angling distal platform 304. In some embodiments, each bend can have a radius of curvature between 0.5 inch and 2 ft. In other embodiments, each bend can have a radius of curvature between 1 inch and 1 ft. In other embodiments, each bend can have a radius of curvature between 3 inches and 9 inches. The distal platform 304 can be angled at an angle α2 with respect to the longitudinal axis L and can be elevated by a height D2 with respect to the horizontal proximal portion of the tubular structure 303. Angle α2 can be between about 0 to 30 degrees, or 5 to 20 degrees, or 10 to 16 degrees. The height D2 can be between about 1 mm to 20 mm. In other embodiments, D2 may be between 3 mm and 10 mm. In other embodiments, D2 may be between 4 mm and 7 mm. In some embodiments, D2 can be approximately equal to the diameter of the vein or blood vessel where the surgical procedure, such as valve creation, is to be performed.

FIG. 4 depicts an embodiment of use of the entire apparatus 400 in a clinical scenario to access a valve creation site 401 and to gain wall apposition. The form from FIG. 3A is used in this example, but this method of use in the body can be applied to all other apparatus described. FIG. 4A depicts over-the-wire 405 access which has been accomplished at the upper thigh 402, below the ilioinguinal ligament, which is the skin puncture site 403. In other embodiments of the method a cut down approach may be used. Other potential skin puncture sites 403 (not depicted) are: above the ilioinguinal ligament, in the thigh just above the saphenofemoral junction, in the mid thigh just below the saphenofemoral junction, in the lower thigh for popliteal vein puncture. A track is made through the skin and tissue down to the vein, at which point a vein puncture site 404 is created using, for example, a needle or trocar with sheath. In some embodiments (not depicted) a puncture element such as a needle or trocar is incorporated into the front of the device itself or is delivered through a through lumen within the device, to be removed after device insertion. FIG. 4B depicts the apparatus 400 being inserted over the wire 405 through both puncture sites 403/404 and advanced into the femoral 406 and popliteal veins 407. FIG. 4C depicts advancement of the apparatus 400 to the distal femoral 406 or popliteal vein 407, so that the distal end is at the valve creation site 401. As can be seen, the shape of the rigid apparatus causes apposition of the device against the anterior portion of the vein wall 408. The shape and rigidity of the apparatus can also be used to create more wall apposition, by rotating the handle 409 as shown in the figure, such that the distal surface of the tubular structure 410 is pivoted upward, with a larger normal force into the anterior surface of the vein 408. This action will force the vein wall to comply with the contour of the distal end of the tubuilar structure 410. FIG. 4D depicts a detailed view of the distal end of the device, and specifically a particular feature of its contour, called a recession 412. This recession is a change in surface height on the side of the device to contact the wall. As depicted in later embodiments, this recession, allows for the tissue to conform to the contour in a way that allows a device exiting a tool lumen 414 to contact the vessel wall at a pre-determined angle α3. In some embodiments, α3 is between 0 degrees and 45 degrees, or between 10 degrees and 35 degrees, or between 15 degrees and 25 degrees.

FIG. 5A depicts an embodiment that comprises a flexible tubular structure 500 instead of a rigid one. This structure 500 can be inserted into a section of a vessel 501 that may contain some element of tortuosity. The tube has within it a communicating lumen 502 that can be used for insertion of a stiffening mechanism 503, which can be advanced toward the distal end 504 of the flexible tubular structure 500, as shown in FIG. 5B. This creates a rigidity of the entire device up to the point of advancement. In some embodiments, the stiffening mechanism 503 can be inserted into the flexible tubular structure 500 after the flexible tubular structure 500 has been inserted into the vessel, causing at least a portion of the vessel to conform to the shape of the stiffening mechanism 503. In some embodiments, at least the distal portion of the stiffening mechanism 503 is substantially straight. In other embodiments, at least the proximal portion of the stiffening mechanism 503 is substantially straight. In some embodiments, the stiffening mechanism 503 may double as an expansion element or visualization mechanism of some kind (see embodiments below).

FIGS. 6A and 6B depict a similar embodiment, in which the stiffening mechanism 600 previously described in FIG. 5 includes a slight bend 601 on the distal portion to aid in advancing it through a tubular structure 602 that has taken at least one bend. The curved stiffening mechanism 600 can be rotated at certain bends until a less resistant path is found to the distal end of the device. The curved section of the stiffening mechanism may be positioned such that when the stiffening mechanism 600 is advanced to the full distal end 603 of the tubular structure 602, a straight section 604 still exists along a sufficient length of vessel 605 for certain techniques of tissue manipulation, such as creation of an autologous valve.

Figure 7:
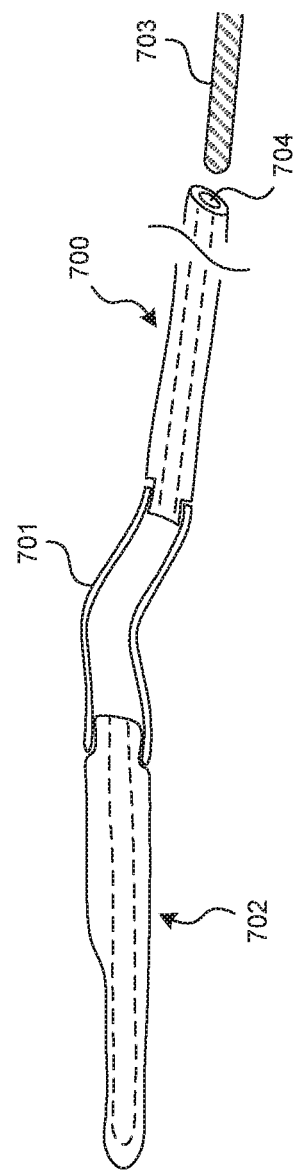
FIG. 7 illustrates another embodiment of a device for accessing a valve creation site.

FIG. 7 depicts an embodiment of the rigid tubular structure 700 that has a short flexible section 701 (about 3 mm to 10 mm in length), which terminates near the distal portion or distal end 702 (about 25 mm to 75 mm) of the rigid tubular structure 700. This allows the device to be more easily advanced through the vasculature and valves by being able to bend around curvatures in the vasculature. A straight rigid stiffening mechanism 703 can be advanced through a communicating lumen 704 to straighten out this flexible section 701 when appropriate. In other similar embodiments, curved stiffening mechanisms (not depicted) can be inserted to causes a specific bend in the flexible section. As described above, in some embodiments, the stiffening mechanisms can have a curved distal portion along with at least one straight section.

In accordance with some embodiments, FIG. 8A depicts a pull wire 800 attached to one side of the flexible distal end 801 of a rigid tubular structure 802. The pull wire 800 can be threaded through the device such that the proximal end of the pull wire 800 remains outside the body and can be manipulated by the user. As depicted in FIG. 8B, when the pull wire 800 is retracted, the distal end 801 of the structure is pivoted upward, causing a larger normal force onto the anterior surface of the vein wall 803. This action will force the vein wall to comply with a recession at the distal end of the tubular structure (not depicted in this figure).

Figure 9A:
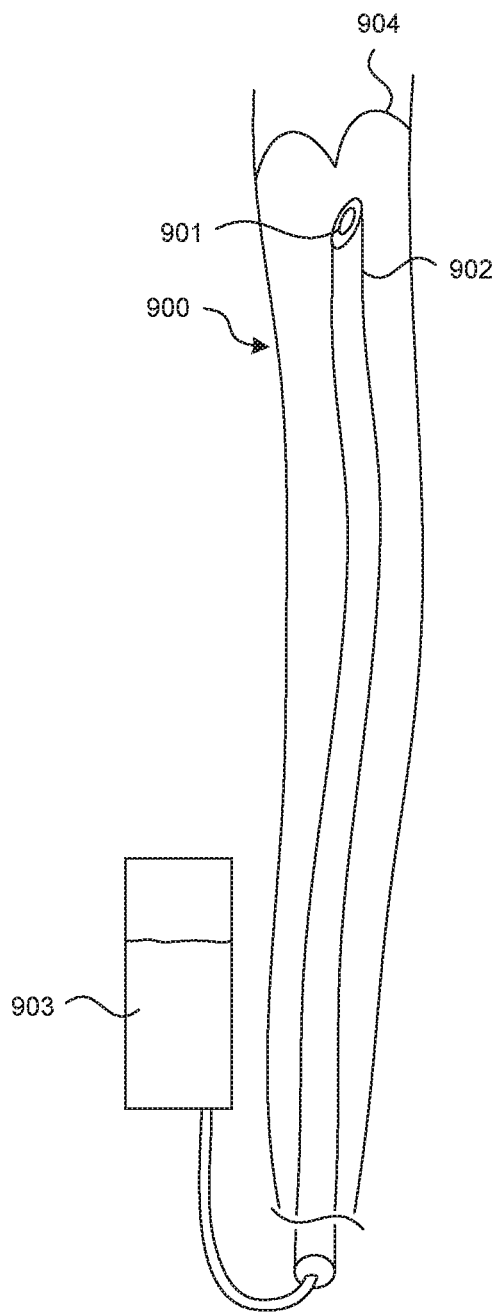
FIGS. 9A-9B illustrate another embodiment of a device and method for straightening out and tensioning a vessel wall.
Figure 9B:
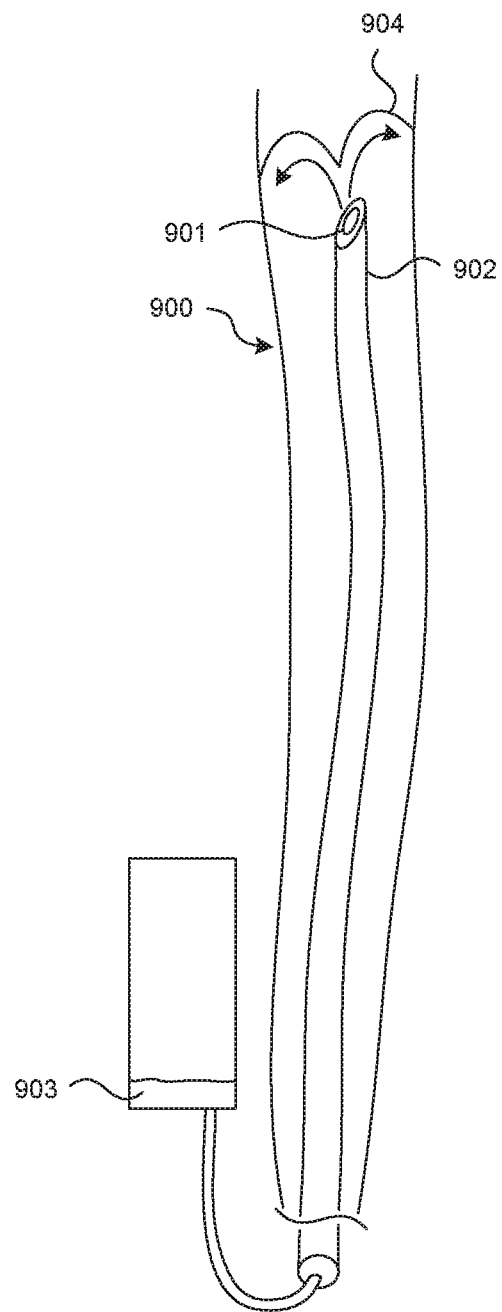

FIG. 9 depicts a different method for straightening out and tensioning a vessel wall 900 in which an exit port 901 at or near the distal end of the tubular structure 902, which is in fluid communication with a fluid source 903, is used to inject a large amount of saline or another fluid into the vessel with enough flow to cause the vessel wall 900 to dilate. In many embodiments, this method can be employed in the venous system above or near an existing valve 904. This method can be used in conjunction with any of the other methods and devices described with which a taut vessel wall is advantageous. In one particular example, this method can be used in conjunction with a puncture device to penetrate a vessel wall 900. In other examples, the devices described above can include a fluid delivery channel and exit port for delivering fluid into the vessel.

Expansion Elements

The following embodiments describe mechanisms that expand from a tubular structure and force the other side of the tubular structure into the vessel wall, which may aid in further procedural steps. All embodiments described for expansion elements (covering FIGS. 10-12, and all associated text that may or may not describe embodiments depicted in figures), can be used in combination with other components described for full valve creation, including but not limited to: locating a valve creation site, hydrodissection, gaining access into an intra-mural space, use of direct or indirect visualization methods, creation of an intra-mural pocket, valve mouth opening, and valve securement for full valve creation. An example of one way in which to combine embodiments to complete the valve creation procedure is depicted in FIG. 19. The embodiments depicted here can be used in combination with these or similar techniques to create a full valve geometry. Another similar example of one way in which to combine embodiments to complete the valve creation procedure is depicted in FIG. 30. The embodiments depicted here can be used in combination with these or similar techniques to create a full valve geometry.

Figure 10:
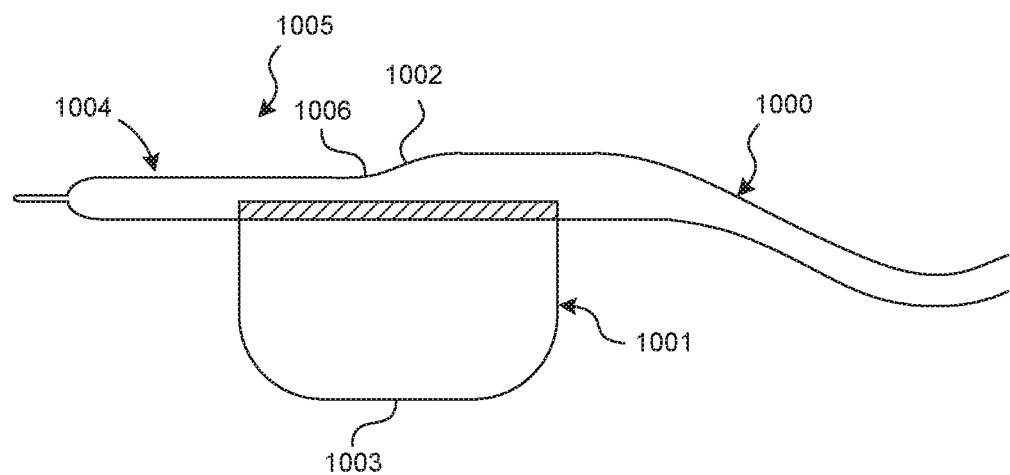
FIG. 10 illustrates an embodiment of a device having an expansion element.

FIG. 10 depicts the rigid tubular structure 1000 with an expansion element 1001, which protrudes off of the opposite side as the tool lumen exit port 1002. In the embodiment shown, the center of the expansion element 1003 in the longitudinal axis is nearly lined up with the exit port 1002 of the tool lumen. In other embodiments, the center point of the expansion element 1003 may be distal or proximal to the exit port 1002 of the tool lumen. In embodiments in which the expansion element is a balloon, an inflation lumen exists (not depicted). In some embodiments of the method, the expansion element 1001 is activated once the apparatus has advanced such that the distal end of the tubular structure 1004 is at the valve creation site 1005. This action will force the vein wall to comply with the recession at the distal end of the tubular structure 1006 and positions the tool lumen exit port 1002 proximal to or against the vein wall.

In some embodiments, the expansion element 1001 is a complaint or semi-compliant balloon bonded directly to the rigid tubular structure 1000 (as shown in FIG. 10).

In some embodiments, the expansion element 1001 is a metal cage or wire made from a shape memory metal such as Nitinol.

Figure 11A:
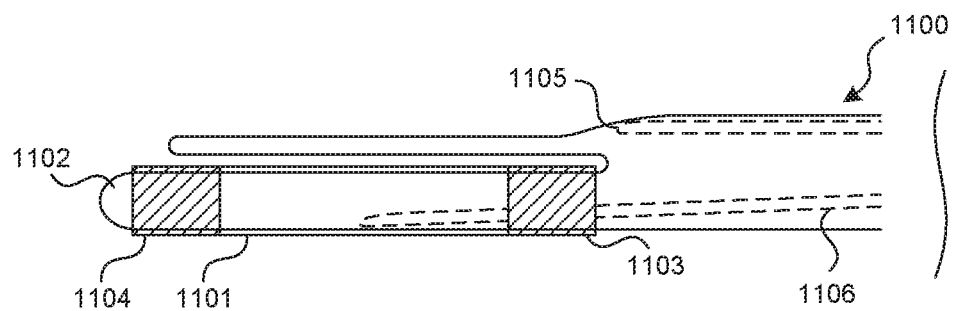
FIGS. 11A-11B illustrate another embodiment of a device having an expansion element.
Figure 11B:
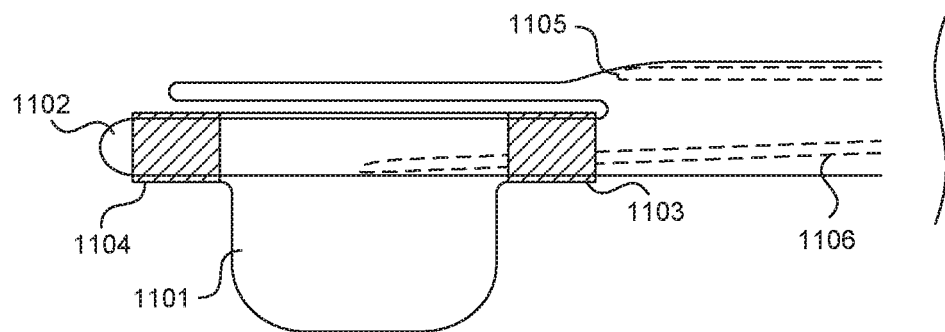

FIG. 11 depicts an alternate embodiment of the tubular member 1100 with expansion mechanism 1101, which comprises a complaint or semi-complaint balloon bonded to a 360 degree or cylindrical protrusion 1102 from the rigid tubular structure 1100, such that a balloon can be bonded circumferentially at the proximal end 1103 and the distal end 1104 of the protrusion 1102, and such that the expansion of the balloon is only permitted in the direction opposite the tool lumen exit port 1105 (FIG. 11B). An inflation lumen 1106 is present for activation of the expansion element.

Figure 12A:
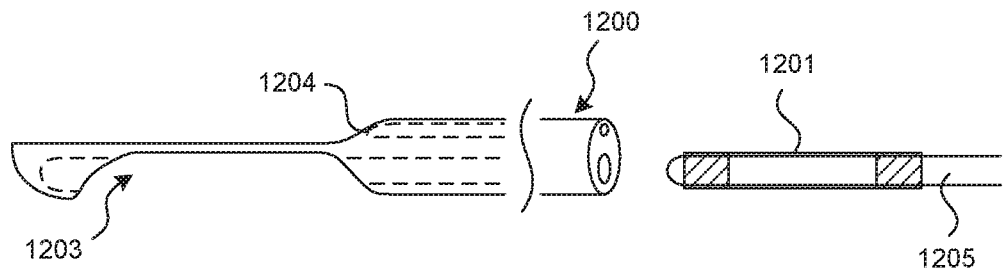
FIGS. 12A-12B illustrate yet another embodiment of a device having an expansion element.
Figure 12B:
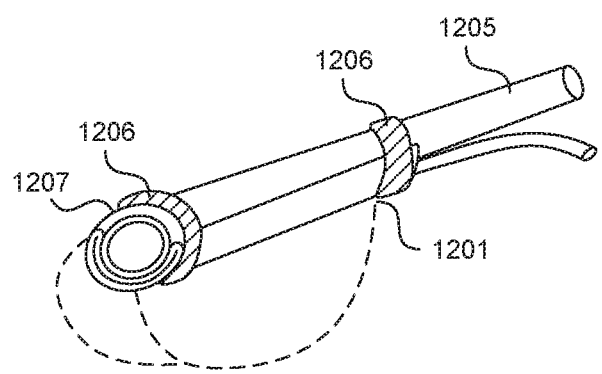

FIG. 12A depicts an alternate embodiment of the tubular structure 1200 with expansion mechanism 1201, which comprises an expansion mechanism lumen 1202 through which a replaceable compliant or semi-compliant balloon or metallic expansion mechanism can be inserted and advanced. The replaceable balloon or metallic expansion mechanism can be attached to the distal portion of a tubular support structure 1205 which can be inserted into the expansion mechanism lumen 1202. Distally, an inflation window 1203 exists on the bottom side of the tubular structure 1200 opposite the tool lumen exit port 1204, such that upon inflation, the expansion mechanism 1201 is forced to expand out of the inflation window 1203 in the direction opposite the exit port of the tool lumen 1204. FIG. 12B depicts one alternate approach to executing this embodiment, which includes an expansion mechanism 1201 folded on the outside of another hollow tubular support structure 1205, with a bonding agent or shrink wrap tubing 1206 sealing off both ends of the expansion member. In this embodiment, the hollow lumen 1207 of the tubular support structure can be used to introduce other tools such as a visualization mechanism.

In some embodiments, the entire distal end of the rigid tubular structure 1200 is made from a stiff silicone, and a silicone balloon which acts as the expansion element 1201 is bonded to the distal end of the rigid tubular structure 1200. This can be made in any of the previously discussed configurations.

In some embodiments, a through lumen exists within the expansion element, which can act as a guidewire lumen if a Seldinger technique is desired.

Puncture Element, Tool Lumen, and Wall Apposition

All embodiments described puncture elements, tool lumens, and wall apposition specifics (covering FIGS. 13-15, and all associated text that may or may not describe embodiments depicted in figures), can be used in combination with other components described for full valve creation, including but not limited to: accessing a valve creation site, use of direct or indirect visualization methods, hydrodissection, creation of an intra-mural pocket, valve mouth opening, and valve securement for full valve creation. An example of one way in which to combine embodiments to complete the valve creation procedure is depicted in FIG. 19. The embodiments depicted here can be used in combination with these or similar techniques to create a full valve geometry. Another similar example of one way in which to combine embodiments to complete the valve creation procedure is depicted in FIG. 30. The embodiments depicted here can be used in combination with these or similar techniques to create a full valve geometry.

FIGS. 13A and 13B depict more detail of another embodiment of the aforementioned rigid tubular structure 1300, which contains within it, a tool lumen 1301, which connects to a proximal opening 1302 on or near the handle 1303 and a distal exit port 1304. Additionally, the rigid tubular structure 1300 contains a through lumen 1305, which connects to a proximal opening 1306 on or near the handle 1303 and a distal exit port 1307. As can be seen, there exists a step down 1308 at the distal exit port of the tool lumen 1304 between the full diameter body of the rigid tubular structure 1300 to the recessed distal surface 1309. FIG. 13C depicts the distal end of the tubular structure from a head on view. In this embodiment it is depicted with a rounded surface 1310 to better accept the curvature of a vessel wall. FIG. 13D depicts a similar embodiment in which the distal end of the tubular structure is flat 1311, which may better assist other follow-on procedural steps such as clearing out the visual field and containment of the hydrodissection bubble.

Figure 14A:
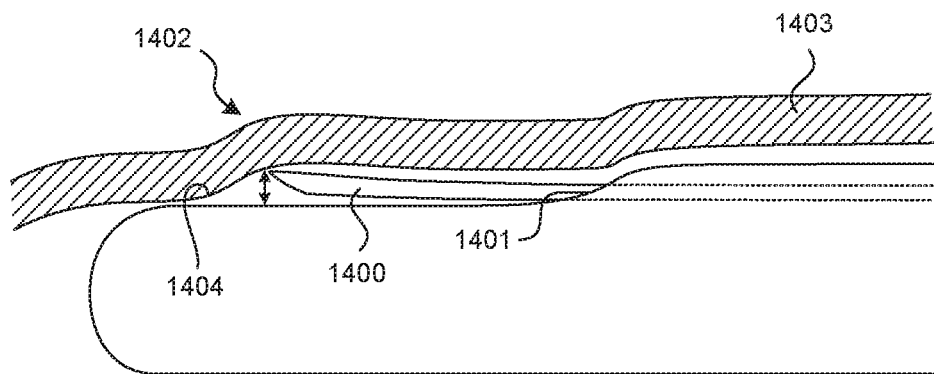
FIGS. 14A-14B illustrate an embodiment of a device for accessing a valve creation site that has a puncture element extending from the tool lumen.
Figure 14B:
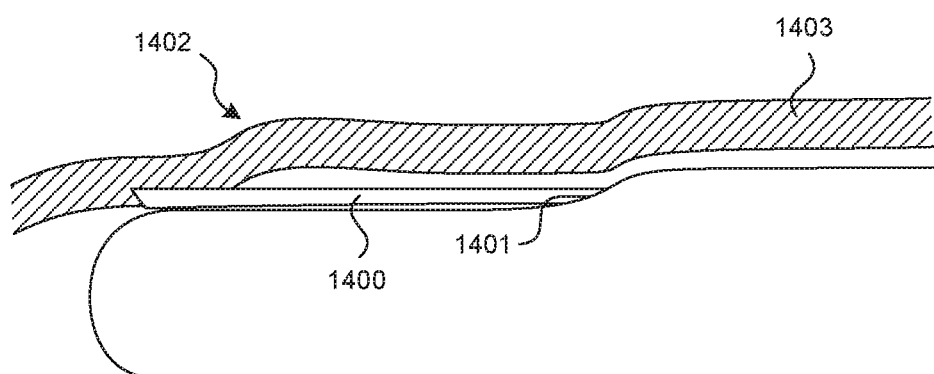

FIG. 14A depicts an embodiment, in which the puncture element 1400 exists outside the tool lumen exit port 1401 prior to advancement of the device to the valve creation location 1402. In this embodiment, the puncture element 1400 can be retracted to the exact location where wall puncture is desired (not depicted), at which point it is advanced into the wall 1403 (FIG. 14B). In this particular embodiment, the puncture height 1404 is determined by the diameter of the puncture element 1400 itself, as well as the bevel geometry and angular orientation of the puncture element 1400. In some embodiments the puncture height 1404 can be between about 0 mm and 3 mm, or 0.2 mm and 1.5 mm, or 0.3 mm and 0.8 mm, or 0.4 mm and 0.6 mm. This is true because the wall apposition created by the device forces the vessel wall 1403 to conform around the puncture element 1400.

Figure 15A:
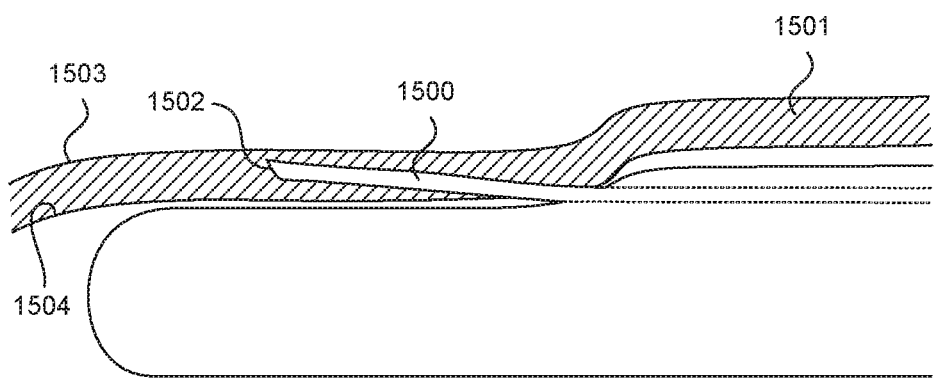
FIGS. 15A-15B illustrate an embodiment of a device for accessing a valve creation site that has a puncture element extending from the tool lumen that can be rotated to control the depth of penetration into the vessel wall.
Figure 15B:
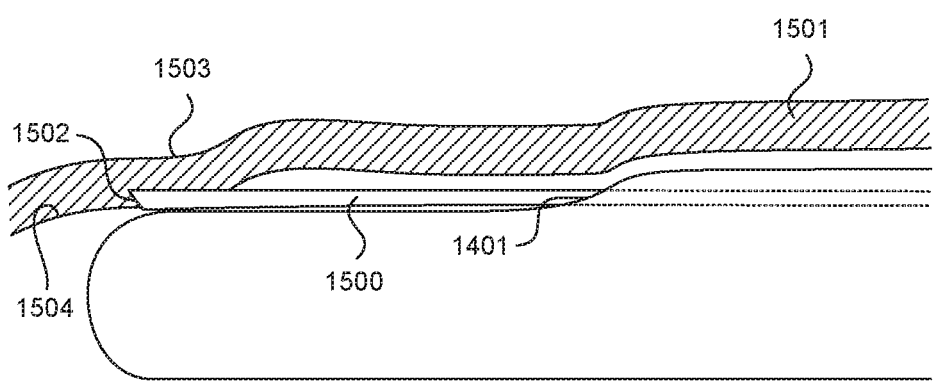

FIG. 15 depicts a method for controlling the depth of the puncture element 1500 within the vessel wall during vessel wall puncture and/or advancement of the puncture element within the vessel wall 1501, with rotation of the bevel 1502 of a puncture element 1500. FIG. 15A depicts how the puncture element 1500 can exhibit forward advancement that tends outward, toward the adventitia 1503 if the bevel 1502 is oriented upward and away from the vessel wall. FIG. 15B depicts how a rotation such that the bevel 1502 is oriented downward toward the intima 1504, can cause the advancement to change course to a more inward path. Angles between these two extremes can be used for more subtle adjustments. In some embodiments (not pictured) a simple dial can be incorporated into the handle to adjust the rotation of the bevel, which intuitively communicates to the user how to tweak for conservative (shallow) or aggressive (deep) puncture or advancement. Also, such a technique may be especially advantageous if used in conjunction with a visualization mechanism (see later embodiments).

Hydrodissection

All embodiments described for hydrodissection (covering FIG. 15, and all associated text that may or may not describe embodiments depicted in figures), can be used in combination with other components described for full valve creation, including but not limited to: locating a valve creation site, creating wall apposition, gaining access into an intra-mural space, use of direct or indirect visualization methods, creation of an intra-mural pocket, valve mouth opening, and valve securement for full valve creation. An example of one way in which to combine embodiments to complete the valve creation procedure is depicted in FIG. 19. The embodiments depicted here can be used in combination with these or similar techniques to create a full valve geometry. Another similar example of one way in which to combine embodiments to complete the valve creation procedure is depicted in FIG. 30. The embodiments depicted here can be used in combination with these or similar techniques to create a full valve geometry.

As is described in previous invention disclosures, advancement of the puncture device can be assisted with infusion of a fluid within the intramural space. In some embodiments, a constant flow of fluid is utilized, such that the same flow rate is ejected from the puncture element at all times. In other similar embodiments, a mechanism only allows fluid to be ejected during the advancement of the puncture element. In other embodiments, the flow rate can be variable and can be adjusted depending on one more parameters, such as the pressure within the vessel or the diameter of the vessel. All embodiments introduced in this invention disclosure can be utilized with previously described techniques for use of hydrodissection to gain access to the intramural space, or to create the full pocket geometry necessary for valve creation.

In an alternate embodiment of hydrodissection, a technique of tissue soaking is described. In this embodiment, a tissue bulking solution such as water for injection, D5W (mixed with glucose), or another solution with low salinity, i.e. a hypotonic solution, is infused into an isolated segment of a vessel. This can be done by inflating two balloons distal and proximal to a potential site, and removing the indwelling blood during infusion of the tissue bulking substance. This solution is allowed to soak the vessel wall for enough time that the tissue expands. Such time may be between 5 seconds and 20 minutes, or between 10 seconds and 5 minutes, or between 20 seconds and 1 minute. This tissue expansion will create a thicker vessel wall and thus will facilitate the techniques described for intramural access.

In some embodiments of the invention, a mechanism for controlling the direction of propagation of a hydrodissection pocket is used. FIG. 15.5A depicts a rigid tubular structure 1500' with distal end 1502' comprised of a specific cross sectional geometry (FIG. 15.5B) with cornered edges 1504' on the side opposite an expandable balloon 1506' (or other expansion mechanism). In this way, when the balloon 1506' is inflated, the flat surface 1508' of the rigid tubular structure 1500' is forced into the vessel wall 1510' in a way that pinches vessel layers tightly together (compressing the wall thickness) along the lines of contact corresponding to the cornered edges 1504'. This occurs along two parallel lines that extend the length of the rigid distal end 1502'. FIG. 15.5A shows a puncture element 1512' emerging from a distal exit port 1514' of a tool lumen, which is submerged within a vessel wall 1510'. The figures also show a hydrodissection agent 1516' which has been injected through the lumen of the puncture element 1512' which forces tissue layers apart within the vessel wall 1510' to create a dissection pocket 1517'. As the agent is injected within the two parallel lines of pinched vessel wall, the dissection pocket 1517' is forced to propagate forward along the length of the vessel wall, as the pinched off lines create a seal and prevent circumferential propagation of the dissection. The geometry of the dissection can thus be dictated by the dimensions of the rigid distal end 1502'. FIG. 15.5C depicts the geometry of hydrodissection pouch that might be created by the device depicted (viewing the vessel wall from above). In some embodiments, the cornered edges 1504' have a radius of curvature (r) between 0" and 0.1", or between 0.00" and 0.01", or between 0.000" and 0.005". The width (w) of the flat surface 1508' may be between 0" and 0.25" or between 0.040" and 0.150" or between 0.080" and 0.120".

FIG. 15.5D depicts another similar embodiment of the distal end of the rigid device 1502' in cross-section. This embodiment comprises a curved transparent viewing window 1518' set between two cornered edges similar to that shown in FIG. 15.5B and included for the same general reasons. This mechanism and technique is then used in combination with other methods and devices described, such as an expansion mechanism, visualization mechanisms and valve creation devices to create an autologous valve.

This mechanisms and techniques described can be used in combination with other methods and devices described, such as a transparent window and visualization mechanisms, valve creation devices, and valve securement mechanisms to create an autologous valve. An example of this entire process is depicted in FIG. 19.

Insertion of Valve Creation Mechanism

Once a puncture element has been introduced into an intramural space to a sufficient depth, a technique is employed to insert a valve creation mechanism into the space. Many embodiments of this technique have been described in previous invention disclosures, all of which can be utilized in combination with new inventions described in this disclosure. Additionally, all embodiments described for inserting a valve creation mechanism or balloon (covering FIGS. 16 and 17, and all associated text that may or may not describe embodiments depicted in figures), can be used in combination with other components described for full valve creation, including but not limited to: locating a valve creation site, creating wall apposition, hydrodissection, gaining access into an intra-mural space, use of direct or indirect visualization methods, creation of an intra-mural pocket, valve mouth opening, and valve securement for full valve creation. An example of one way in which to combine embodiments to complete the valve creation procedure is depicted in FIG. 19. The embodiments depicted here can be used in combination with these or similar techniques to create a full valve geometry. Another similar example of one way in which to combine embodiments to complete the valve creation procedure is depicted in FIG. 30. The embodiments depicted here can be used in combination with these or similar techniques to create a full valve geometry.

Figure 16:
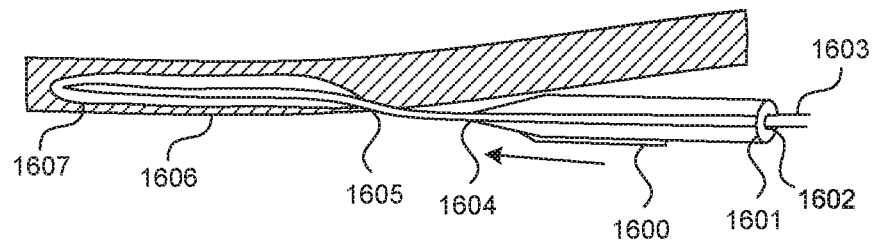
FIG. 16 illustrates an embodiment of a valve creation mechanism being inserted into a vessel wall.

One embodiment consistent with the valve creation technique described thus far in this application, is an "over the wire" approach to insertion of a valve creation mechanism, with the puncture element acting as the "wire" in this description. FIG. 16 depicts a mechanism, which includes a deflated non-compliant balloon 1600, which exists on a tube 1601 with a hollow lumen 1602 within, sized to accommodate the puncture element 1603 with a tight sliding fit. A feather tapered tip 1604 at the distal end of the balloon tube 1601 is implemented to assist the device in entering through the hole 1605 in the intimal wall 1606. This mechanism can be inserted until it reaches the full depth of the intramural pocket 1607, and then it is expanded to form a full valve flap geometry by separating tissue layers and by opening up the intimal hole at the top of the pocket. In the embodiment depicted, the rest of the tubular structure is removed prior to advancement of the valve creation mechanism over the puncture element. This can be done by implementing a removable luer on the back-end of the puncture element 1603, so that the entire device can be removed while the puncture element remains embedded in the vessel wall.

Figure 17A:
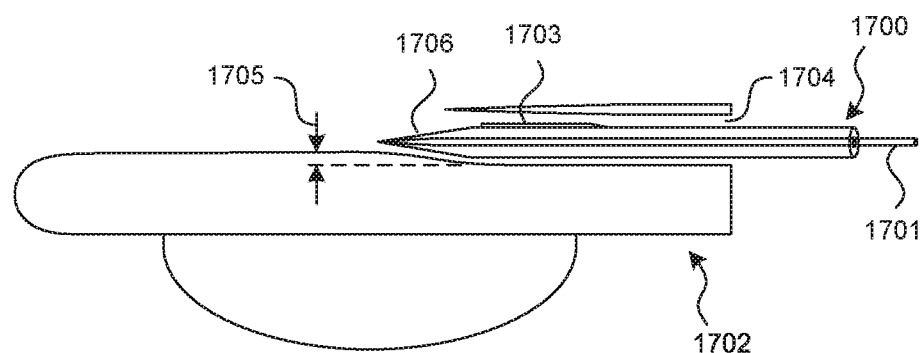
FIG. 17A-17B illustrate another embodiment of a valve creation mechanism.
Figure 17B:
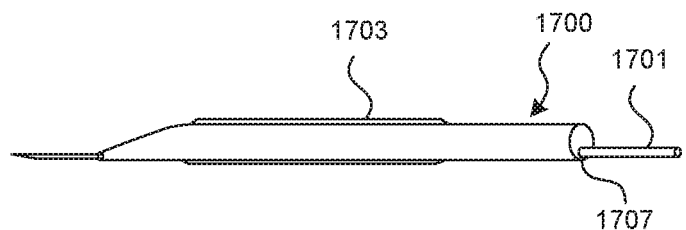

FIG. 17A depicts an alternate embodiment in which the same technique for introducing a valve creation mechanism 1700 (depicted here with a deflated and non-compliant balloon 1703) over the puncture element 1701 is utilized, but in this embodiment the valve creation mechanism 1700 is incorporated into the tubular structure 1702 with expansion mechanism 1703, so that it can be advanced into the vessel wall without removing the tubular structure. This is accomplished with a larger diameter tool lumen 1704. In this embodiment, the puncture element 1701 is free to advance separate from the valve creation mechanism 1700 to find the correct intramural plane. Then, the valve creation mechanism 1700, which is pre-loaded onto the puncture element 1701 (as shown), is advanced over the puncture element 1701 as described previously. As can be seen, an off-set 1705 is built in so that the puncture element 1701 remains at a proper puncture height, despite being supported by the lumen 1704 of the valve creation mechanism 1700. In some embodiments, the off-set is between about 0 mm and 2 mm, or between 0.5 mm and 1.5 mm, or between 0.75 mm and 1.25 mm. A flexibility of material is utilized around this tool lumen exit port 1706 and within the valve creation mechanism 1700, to allow it to deform enough to exit the tool lumen exit port 1706 in the presence of the off-set 1705. FIG. 17B depicts a similar method of use, but the valve creation mechanism 1700 includes an offset puncture element lumen 1707, so that the off-set 1705 on the tubular structure 1702 can be minimized or reduced.

Valve Fixation

Once a valve flap (monocuspid) or two adjacent valve flaps (bicuspid) are created within a vessel, it may be advantageous to affix them to a vessel wall or an adjacent valve flap to prevent re-adherance. All embodiments described for valve fixation (covering FIGS. 18-19, and all associated text that may or may not describe embodiments depicted in figures), can be used in combination with other components described for full valve creation, including but not limited to: locating a valve creation site, creating wall apposition, hydrodissection, gaining access into an intra-mural space, use of direct or indirect visualization methods, creation of an intra-mural pocket, and valve mouth opening. An example of one way in which to combine embodiments to complete the valve creation procedure is depicted in FIG. 30. The embodiments depicted here can be used in combination with these or similar techniques to create a full valve geometry.

Figure 18D:
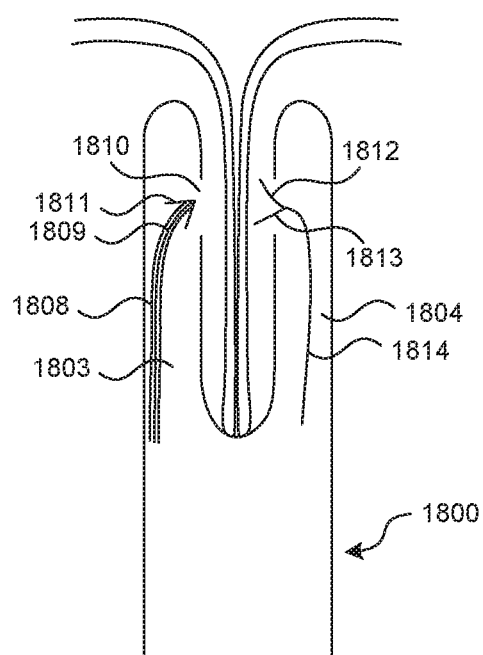

FIG. 18 depicts one method and mechanism for fixation in a bicuspid valve creation technique. As depicted in FIG. 18A, the fixation mechanism 1800 contains two lumens, which extend through the main shaft 1801. At the distal end, two hinged tongs extend in a "V" shape from the shaft. One lumen 1802 connects to the left tong 1803, the other lumen 1804 connects to the right tong 1805. Both lumens terminate at a sideways and inwardly facing exit port 1810, 1812, which are aligned. In this method for use, as depicted in FIG. 18B the fixation mechanism 1800 is advanced to align the valve cusps 1806 against a stopper mechanism 1807, which can be located at the base of the v portion of the tongs. This allows for some deviation in longitudinal location of the adjacent valves. At this point, the tongs are closed (depicted in FIG. 18C) to secure the leaflets 1806 in the place. Then, depicted in FIG. 18D, a semi-stiff tube 1808 containing a suture 1809 is pushed through the incoming lumen 1802 until it makes the bend and exits the left exit port 1810. The tube has on it a sharp distal end 1811. The sharp point 1811 punctures the two leaflets 1806, and is then accepted by an accepting mechanism 1812 present at the entrance 1813 to the outgoing lumen 1804. Once the sharp tip 1811 is captured, a pull wire 1814 pre-loaded in the outgoing lumen 1804 is pulled outward, creating a full loop of suture (once the stiff tube is removed), that tracks through both leaflets. A knot can then be tied form the outside, and can be transmitted through a slot 1815 (FIG. 18A) between the lumens toward the leaflets and left in place. A cutting mechanism (not depicted) is present to cut the slack ends.

FIG. 19 depicts another similar embodiment for a monocuspid valve fixation technique. As shown in FIGS. 19A and 19G, a mechanism for fixing the valve can be disposed within a tool lumen 1908 of the valve creation mechanism 1902. The valve creation mechanism 1902 is a tubular structure with a uni-directional balloon 1904 bonded proximally and distally to one side of the shaft, such that when inflated through an inflation lumen 1906, the balloon 1904 expands outward from one side of the valve creation mechanism 1902 (see FIG. 19B). In some embodiments, the tubular structure can have a tapering distal portion. In some embodiments, the taper can be asymmetrical such that the tapering portion is located on the same side as the balloon 1904. The valve fixation mechanism is delivered through a tool lumen 1908, which is fluidly connected to the proximal end 1910 and a distal exit port 1912. In some embodiments, the tool lumen 1908 can be located within the tubular structure on the opposite side as the balloon such that the distal exit port 1912 is located at the end of the tapering portion. Additionally, there exists a sideways facing exit port 1914 at a location opposite the balloon 1904, near the distal end of the tubular mechanism. The sideways facing exit port 1914 may be located between 0 mm and 8 mm distal to the most proximal part of the expandable portion 1916 of the balloon 1904. Or, it may be located between 1 mm and 5 mm distal to the most proximal part of the expandable portion 1916 of the balloon 1904. Or, it may be located between 2 mm and 4 mm distal to the most proximal part of the expandable portion 1916 of the balloon 1904. In this embodiment, the tool lumen 1908 doubles as a channel for the puncture element 1918 and for the valve fixation mechanism 1900. In other embodiments, the tubular structure of the valve creation mechanism 1902 can have a separate tool lumen 1908 and puncture element lumen (not shown).

Figure 19E:
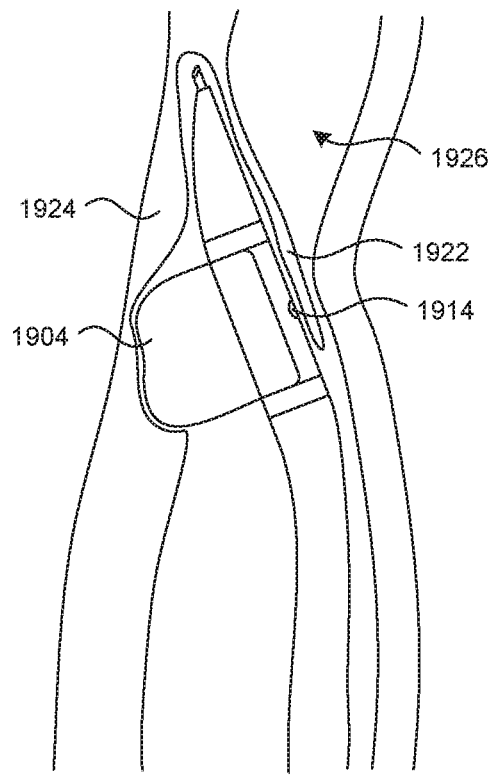
Figure 19F:
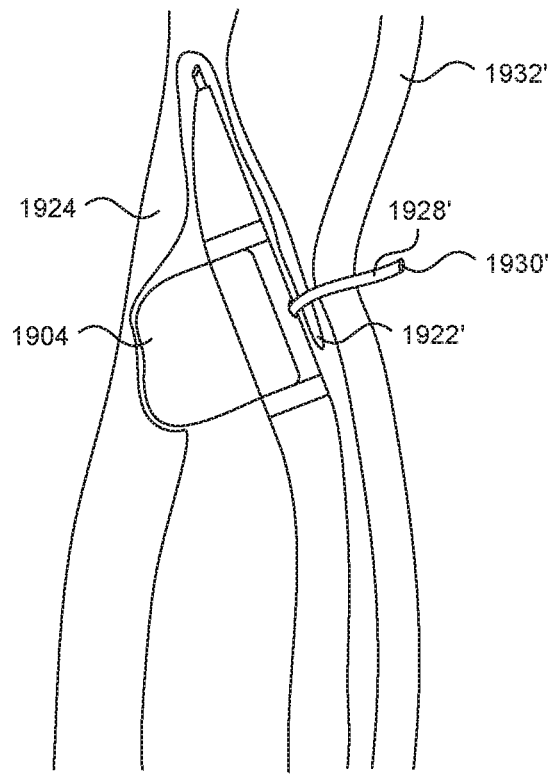
Figure 19G:
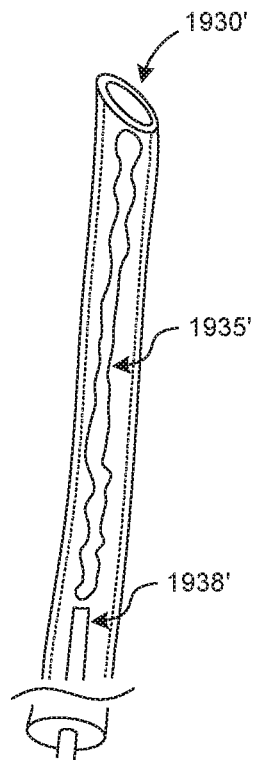
Figure 19H:
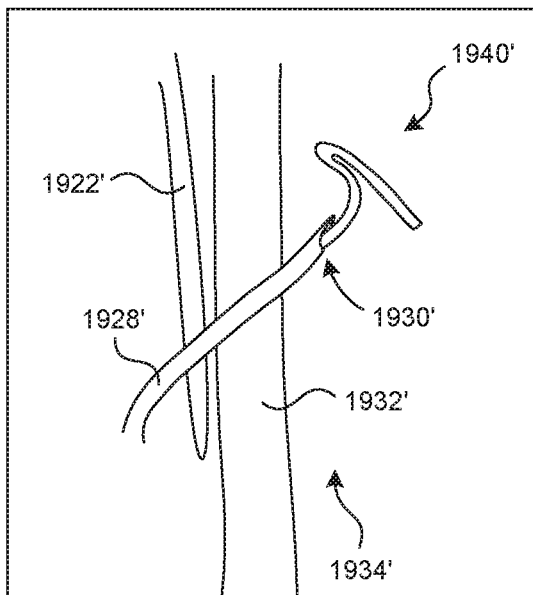
Figure 19I:
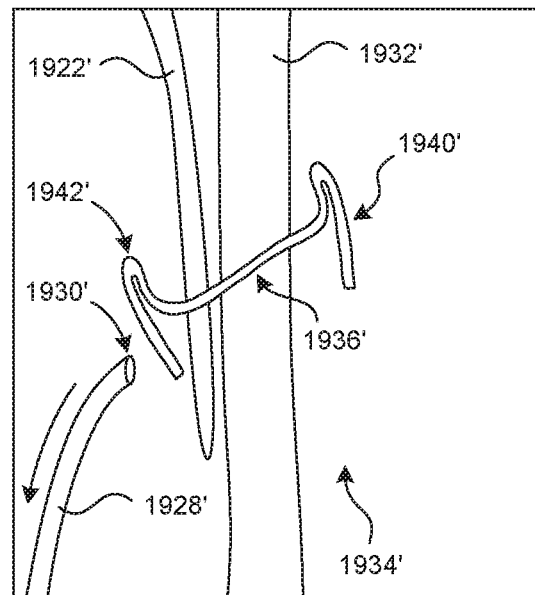

As is shown in FIG. 19C, the puncture element 1918 is used to create a dissection pouch 1920 within the vessel wall. As shown in FIG. 19D, the valve creation mechanism 1902 is then advanced over the puncture element 1918 into the pouch 1920. As shown in FIG. 19E, the balloon 1904 is then inflated to create the valvular flap 1922. The device can be oriented with the balloon facing outward, toward the vessel wall 1924, such that the sideways facing exit port 1914 is facing inward toward the lumen 1926. In some embodiments of the method, the balloon 1904 may be oriented inward toward the lumen 1926 upon inflation, and then it is rotated about 180 degrees after inflation. Prior to activating the valve fixation mechanism, the sideways facing exit port 1914 should be apposed to the valvular flap 1922 as shown in FIG. 19E. At this point, a curved puncture element 1928 is advanced to the sideways facing exit port 1914. This puncture element has a sharp distal end 1930, and has a built-in curvature to allow it to exit the sideways facing exit port 1914 when advanced. This may be made from a shape memory material such as Nitinol, or from stainless steel or another rigid metal or plastic. In this embodiment, when the curved puncture element 1928 is advanced, it punctures through the valvular flap 1922 and through the opposing vessel wall 1932, such that the sharp distal end 1930 extends into or near the extravascular space 1934 (see FIG. 19F). The valve fixation mechanism also comprises a pre formed "H" tag implant 1936 and a push rod 1938. The pre-formed "H" tag 1936 is made from a shape memory material such as Nitinol, and is forced into an unnatural straight configuration when inside the lumen of the curved puncture element 1928 (see FIG. 19G). The pre-formed "H" tag 1936 can be pushed distally with the rigid push rod 1938. FIG. 19H depicts what happens as the push rod 1938 is advanced, and the distal end 1940 of the "H" tag 1936 as it exits the distal sharp point 1930, and takes its natural barred shape in the extravascular space 1934. FIG. 19I depicts how upon removal of the curved puncture element 1928, the "H" tag remains in place, and the proximal end 1942 of the "H" tag 1936 takes its natural barred shape on the inside of the valvular flap 1922. At this point, the balloon 1904 can be deflated, and the entire device can be removed (not depicted), leaving the "H" tag 1936 in place, which acts to prevent the flap from re-adhering to the vessel wall from which it came.

In another similar embodiment, the curved puncture element 1928 is curved enough to exit the sideways facing exit port 1914, and re-enter another sideways facing exit port (not depicted). In this embodiment, a suture is passed through the puncture element 1928, and can be knotted or cauterized or bound into a loop geometry once the curved puncture element 1928 is passed through the valvular flap 1922 and the vessel wall 1932, and then is re-entered through the valvular wall 1932 and flap 1922 again.

The previously described monocuspid valve fixation techniques could also be applied to a bicuspid valve fixation technique, where the valve creation mechanism 1902 can be used to create a second valvular flap opposite the first valvular flap, and the valve fixation mechanism can be used to secure the two valvular flaps together. Similarly, the previously described valve fixation techniques can be applied to a tricuspid valve fixation technique by creating and securing a third valvular flap.

Direct Visualization

In some embodiments of the invention, the use of direct visualization may be advantageous during vein access, advancement to the valve creation site, determination of which valve creation site to use, the valve creation procedure, and for confirmation of success following the procedure. The figures shown, display a variety of embodiments. Each embodiment of the direct visualization mechanism (covering FIGS. 20-22, and all associated text that may or may not describe embodiments depicted in figures) can be combined with previously described embodiments of other features such as locating a valve creation site, creating wall apposition, hydrodissection, gaining access into an intra-mural space, use of indirect visualization methods, creation of an intra-mural pocket, and valve mouth opening, regardless of if they are depicted in each individual figure. An example of one way in which to combine these embodiments to complete the valve creation procedure is depicted in FIG. 19. The embodiments depicted here can be used in combination with these or similar techniques to create a full valve geometry. Another similar example of one way in which to combine embodiments to complete the valve creation procedure is depicted in FIG. 30. The embodiments depicted here can be used in combination with these or similar techniques to create a full valve geometry.

Figure 20:
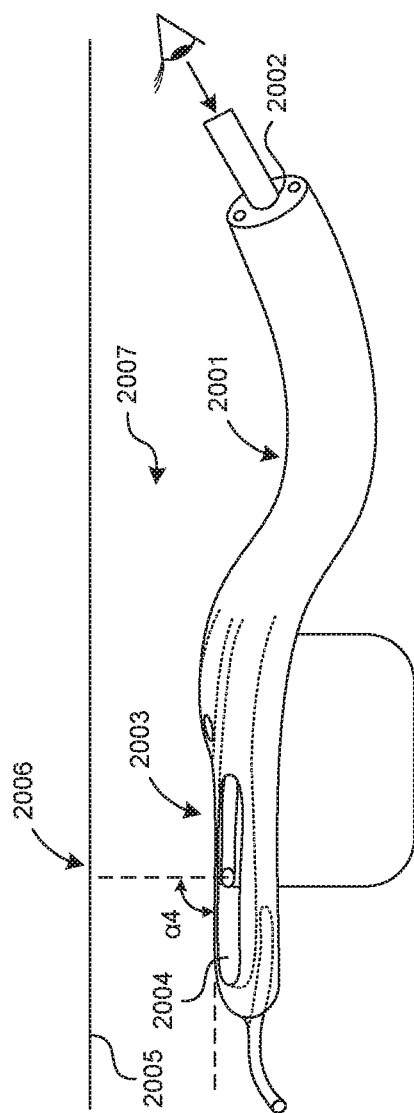
FIG. 20 illustrates an embodiment of a direct visualization mechanism.

FIG. 20 depicts the use of a direct visualization mechanism 2000 incorporated into the flexible or rigid apparatus 2001 described herein. An additional lumen, called the visualization lumen 2002, is depicted, which allows a visualization mechanism 2000 (depicted here as a flexible scope) to be advanced up to the distal end of the tubular structure 2003. Also, present in this embodiment, is a viewing window 2004 at the distal end of the tubular structure 2003, which opens upward toward the vessel wall 2005 and extends along the length of the valve creation site 2006 to allow for a visualization mechanism that can deflect an image to some angle to see through the device and into the vessel lumen 2007 and toward the vessel wall 2005. Deflection angle, $\alpha 4$, is the angle that the center of the visual field takes with the axis of the distal end of the tubular structure (which is more or less parallel to the vessel wall). A 0 degree deflection would correspond to visualization close to a head on view (straight down the lumen of the vessel). A 90-degree deflection angle (as depicted in FIG. 20), refers to an angle of visualization that is directly perpendicular to the vessel wall. In some embodiments, $\alpha 4$ can be between 0 degrees and 145 degrees, or between 8 degrees and 120 degrees, or between 30 degrees and 90 degrees, or between 50 degrees and 75 degrees.

In some embodiments, the visualization mechanism 2000 can be a fiber optic device.

In some embodiments, the visualization mechanism 2000 can be a rod and lens system, rigid device.

In some embodiments, the visualization mechanism 2000 can be advanced and retracted along the distal end of the tubular structure to adjust the viewing location.

In other embodiments, the rigid apparatus 2001 takes a linear form, with a visualization lumen 2002, such that off-the-shelf rigid scopes can be inserted up to the viewing window 2004 for use with this device.

In other embodiments, the tubular structure is flexible or has a flexible section, but is made stiff by insertion of a rigid visualization mechanism 2000.

In some embodiments, the visualization mechanism used allows for a 90-degree deflection angle on the line of sight near the distal end of the mechanism. Other embodiments may utilize a 45-degree deflection angle. Other embodiments may utilize a 30-degree deflection angle. Other embodiments may utilize any other deflection angle between 0-degrees and 180-degrees, inclusive.

Figure 21A:
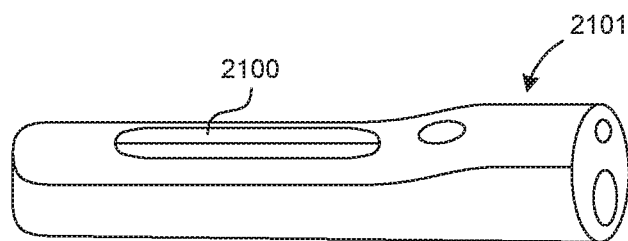
FIGS. 21A-21C illustrate various embodiments of a viewing window that can be used with a direct visualization mechanism.
Figure 21B:
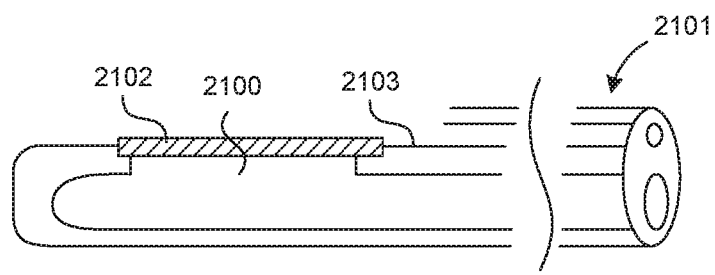
Figure 21C:
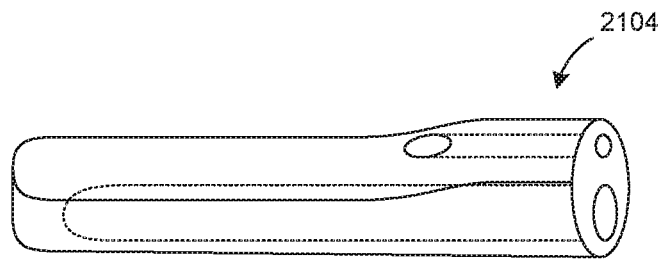

FIG. 21 depicts different embodiments of the viewing window 2100 described. FIG. 21A depicts a viewing window 2100 that is simply a slot or hole in the rigid tubular structure itself 2101. FIG. 21B depicts the use of a transparent plate or film 2102 made of glass, plastic or another transparent material, which rests within the viewing window 2100 flush or nearly flush with the rest of the surface of the tubular structure 2103. This transparent plate 2102 can act as a transparent medium for viewing as well as a landing area for the vessel wall to rest during the puncture process. FIG. 21C depicts an embodiment in which the distal end of the tubular structure 2104 is itself made from a transparent material.

Figure 22A:
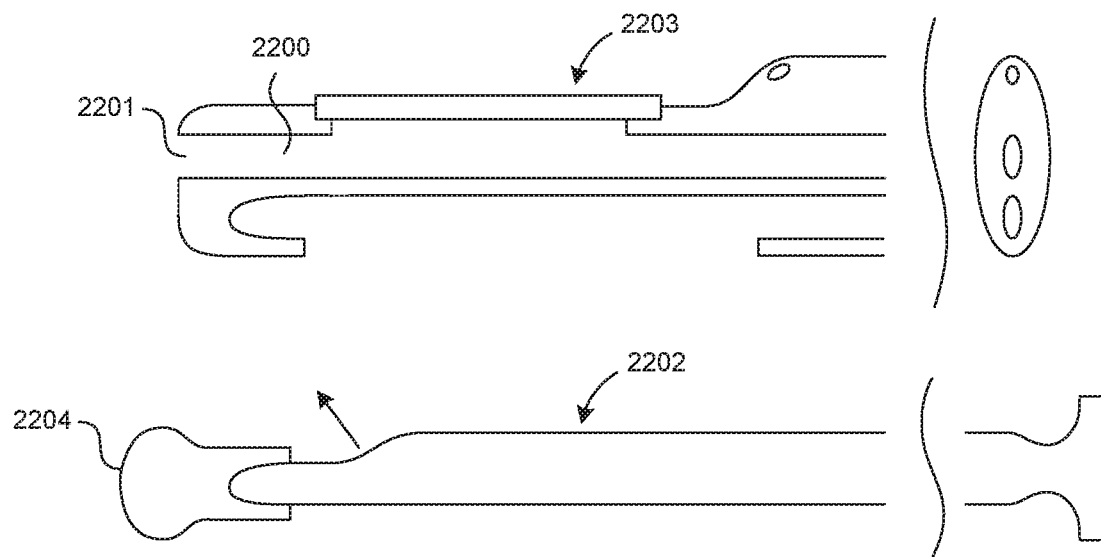
FIGS. 22A-22B illustrate various embodiments of a visualization mechanism.
Figure 22B:
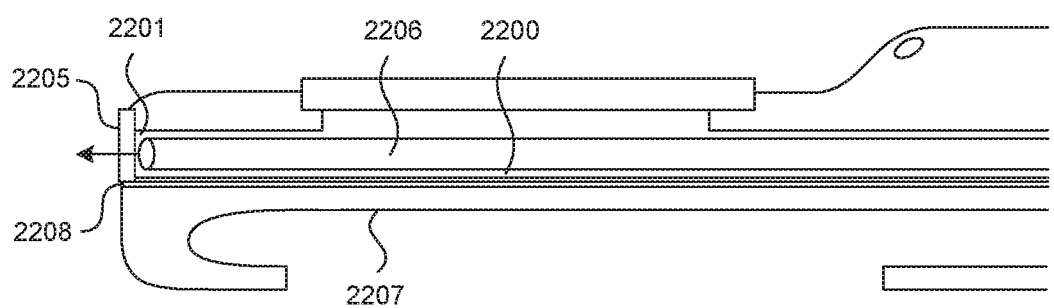

FIG. 22A depicts an embodiment in which the visualization lumen 2200 has an open distal end 2201. In this way, a forward facing visualization mechanism (not depicted) may be advanced to the very distal end of the device 2201, or past the distal end of the device to see forward. This may be beneficial for navigating through existing venous valves. Then at a different time, the forward facing visualization mechanism can be removed and an angled visualization mechanism 2202 can be inserted to the viewing window 2203 to view the vessel wall during the procedure. Also in this figure, there exists an angled visualization mechanism 2202 (shown as a rigid scope) attached to a blood stopper 2204 at its distal end, which may be beneficial for flushing blood from the visualization lumen 2200, and for preventing blood from entering the lumen, in this particular embodiment. FIG. 22B depicts an alternate similar embodiment, in which a clear forward facing window 2205 exists at the end of the open front end 2201 of the visualization lumen 2200, to allow for forward facing direct visualization 2206 without allowing for blood or other foreign fluids to enter the visualization lumen 2200. Also included in this embodiment is a forward facing flush lumen 2207, shown here with an exit port 2208 directly below the clear forward facing window 2205. This would allow the user to flush clear saline in front of the forward facing visualization mechanism 2206 to aid in seeing through opaque blood. Additionally this lumen 2207 could double as a guidewire lumen to further assist in access.

Direct Visualization Assisting Mechanisms

Due to the opacity of blood, direct visualization may require an assist mechanism to help clarify the field of view. All embodiments described for assisting in direct visualization (covering FIGS. 23-26, and all associated text that may or may not describe embodiments depicted in figures), can be used in combination with other components described for full valve creation, including but not limited to: locating a valve creation site, creating wall apposition, hydrodissection, gaining access into an intra-mural space, use of indirect visualization methods, creation of an intra-mural pocket, valve mouth opening, and valve fixation. An example of one way in which to combine these embodiments to complete the valve creation procedure is depicted in FIG. 19. The embodiments depicted here can be used in combination with these or similar techniques to create a full valve geometry. Another similar example of one way in which to combine embodiments to complete the valve creation procedure is depicted in FIG. 30. The embodiments depicted here can be used in combination with these or similar techniques to create a full valve geometry.

FIG. 23A depicts a visualization assisting mechanism involving a flushing lumen 2300, which is fluidly connected to a flushing fluid source proximally and a flushing lumen exit nozzle or port 2301 at or near the distal end of the rigid tubular structure 2302. In the embodiment depicted, the fluid is flushed across the viewing window 2303 from its distal end toward the tool lumen exit port 2304 in a proximal direction. This flushing direction may be advantageous, as it is in the direction of blood flow, and may aid in clearing the visual field.

FIG. 23B depicts a visualization assisting mechanism involving a flushing lumen 2300, which is fluidly connected to a flushing fluid source proximally and a flushing lumen exit nozzle 2301 at or near the distal end of the rigid tubular structure 2302. In the embodiment depicted, the flushing lumen 2300 is right next to the tool lumen 2305 and fluid is flushed across the viewing window 2303 from its proximal end toward the distal end of the device. This flushing direction may be advantageous, as it is may be very easy to incorporate into the manufacturing design.

In another embodiment of a device and a method of use (not depicted), a visualization assisting mechanism is embodied by a flushing lumen 2300, which is the same as the tool lumen 2305, and a flushing lumen exit nozzle 2301 which is the same as the tool lumen exit port 2304. In this way, the act of hydrodissection, or a flushing of the lumen prior to, during, and after puncture can be used to clear the field of view. In a similar embodiment, flushing is done through the puncture element itself (not depicted).

In another embodiment (not depicted), a flushing lumen exit nozzle 2301 exists beside the viewing window 2303, such that a flush can occur across the window in a perpendicular direction to the direction of the puncture element movement. This may be advantageous for clearing blood that is trapped between the window 2303 and the vessel wall.

Figure 24:
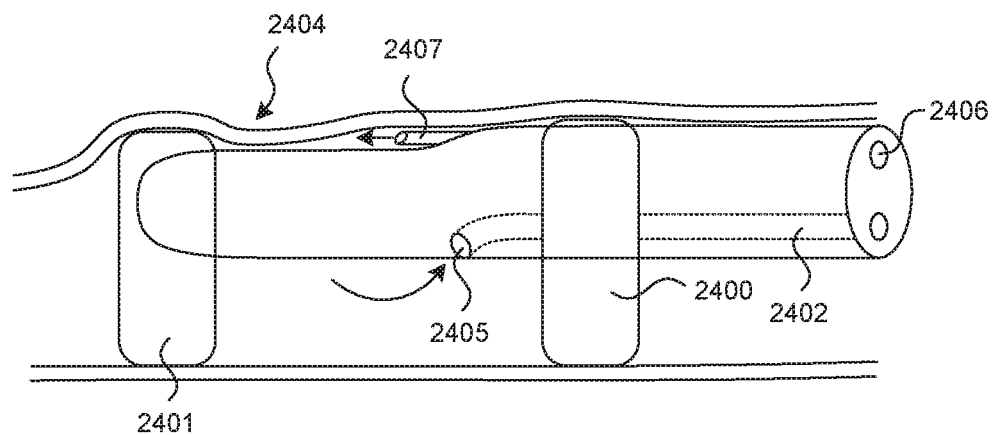
FIG. 24 illustrates another embodiment of a visualization assisting mechanism.

FIG. 24 depicts an embodiment in which two expansion elements 2400/2401 and a fluid removal lumen 2402 are used to evacuate a segment of vessel 2403 of blood. As is shown, the two expansion elements 2400/2401 (depicted as balloons) are expanded proximal and distal to the valve creation site 2404. At that point blood is removed from the vessel between the balloons through the suction lumen exit port 2405 with the presence of a negative pressure source fluidly connected to the suction lumen 2402. As blood is evacuated, saline or another clear fluid is introduced through an infusion channel 2406 or the puncture element 2407 at the same rate into the vessel, such that the vessel maintains its dilated form, but the fluid is transparent for viewing purposes.

Figure 25:
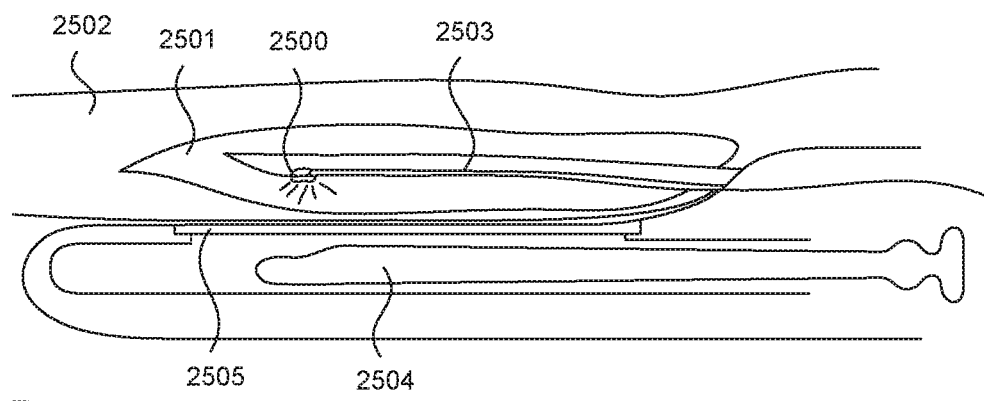
FIG. 25 illustrates an embodiment of a puncture element identifier.

FIG. 25 depicts a puncture element identifier 2500, which helps the user see where the tip of the puncture element 2501 is, even if it is within the vessel wall 2502. In the embodiment shown, the puncture element identifier 2500 is a small light source such as an LED or the output of a fiber optic cable 2503. The identifier may reside at the base of the bevel (as shown), or somewhere else along the bottom shaft of the puncture element 2501, within about 3 mm of the distal end. In this way, a direct visualization mechanism, shown here as an angled scope 2504 looking through a transparent window 2505, which is in contact with the vessel wall 2502. In another similar embodiment, two or more identifiers 2500 are located on different sides of the puncture element 2501, so that the puncture element 2501 can be identified no matter what angular orientation it has.

In other similar embodiments, the puncture element identifier 2500 is simply a non-powered reflective surface. In other embodiments, the identifier 2500 is an ultrasound transducer.

Figure 26A:
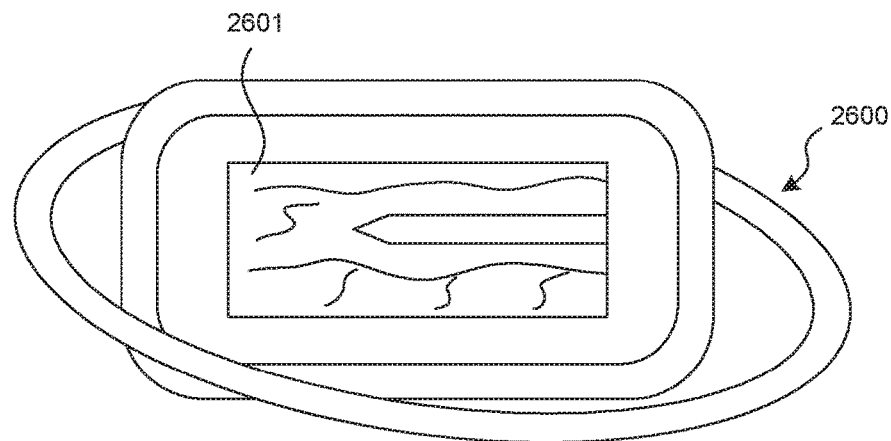
FIGS. 26A-26C illustrate various embodiments of visualization displays that communicate the image from a visualization mechanism to the user.
Figure 26B:
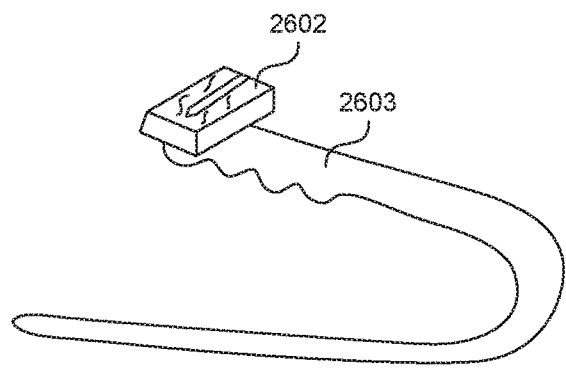
Figure 26C:
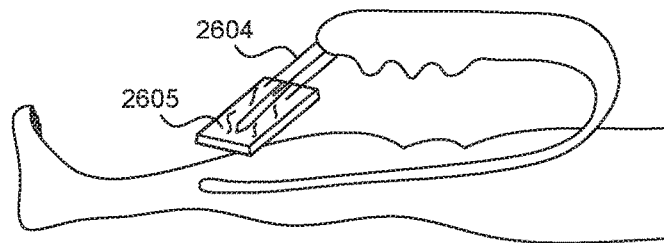

The invention also includes embodiments of visualization displays which are used to communicate the image from a visualization mechanism to the user. FIG. 26A depicts the use of a headset 2600, which displays the image to the user within the eyepiece 2601 of the set. FIG. 26B depicts the use of a small screen 2602 attached to the handle 2603 of the device, which displays the image. FIG. 26C depicts the use of a projection of the image 2604 from the device onto the patient or any flat surface 2605 external to the patient. In some embodiments the image is transmitted wirelessly or through a wired communication to a smart phone or customized mobile device, with sterilization maintained by a protective pouch. In some embodiments a stand-alone monitor such as a tv set or another type of mobile capital equipment is used.

Ultra Sound Based Visualization Assisting Mechanisms

In some embodiments, the use of external ultrasound visualization is used for multiple functions including but not limited to determination of potential valve creation sites, vein access and advancement to the valve creation site, the valve creation procedure, and for confirmation of success following the procedure. The figures shown display a variety of embodiments. All embodiments described for ultra sound based visualization assisting mechanisms (covering FIGS. 27-28, and all associated text that may or may not describe embodiments depicted in figures), can be used in combination with other components described for full valve creation, including but not limited to: locating a valve creation site, creating wall apposition, hydrodissection, gaining access into an intra-mural space, use of direct or indirect visualization methods, creation of an intra-mural pocket, valve mouth opening, and valve fixation. An example of one way in which to combine these embodiments to complete the valve creation procedure is depicted in FIG. 19. The embodiments depicted here can be used in combination with these or similar techniques to create a full valve geometry. Another similar example of one way in which to combine embodiments to complete the valve creation procedure is depicted in FIG. 30. The embodiments depicted here can be used in combination with these or similar techniques to create a full valve geometry.

Figure 27C:
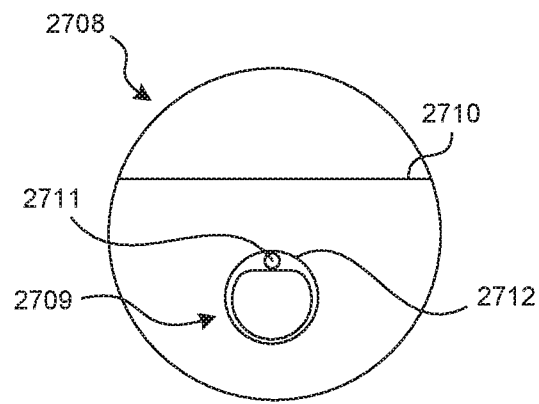
Figure 27D:
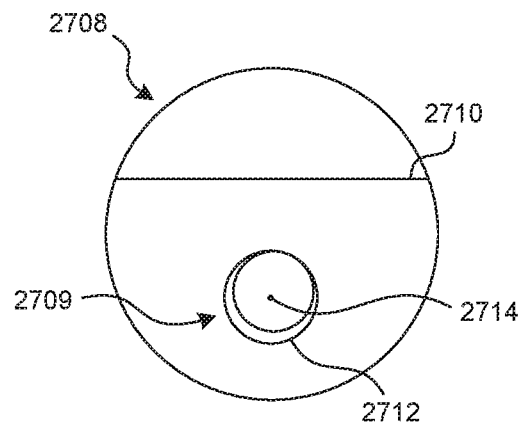

FIG. 27 depicts use of an external ultrasound probe 2700, used with specific settings for optimal resolution in the deep veins or other vessels of choice. As can be seen in FIG. 27A, the unit is used up and down the patient's leg 2701 (or over whatever body part is to be treated), until a viable valve creation site is identified. The user may look for a segment of vessel with a constant or nearly constant thickness wall 2702, as compared to images of planes immediately proximal and distal to the current plane. If the user finds an unevenly thickened location 2703, he/she will know to move to a different location. FIG. 27B depicts how once the cleanest, most consistent vessel wall location is identified, a marker 2704 is placed at the correct location on the skin 2705. At this point, in some embodiments the device is advanced into the vessel until a positioning handle marker 2706 is aligned with skin marker 2704, where the handle marker 2706 corresponds to the location of the distal end of the device. At this point, the user may check with ultrasound to confirm that the device is properly located. Finally, the probe can be maintained at the correct location for the duration of the procedure. In this way, the ultrasound image 2708 can be utilized to visualize the patient's vessel 2709 some distance below the patient's skin 2710. The image can be used to determine placement of the puncture element 2711 within the vessel wall 2712 (FIG. 27C), size and length of hydrodissection pocket, placement of the valve creation expansion mechanism, execution of valve creation with expansion mechanism 2714 (FIG. 27D), execution of valve fixation, and finally evaluation of valve dynamics after creation.

Figure 28:
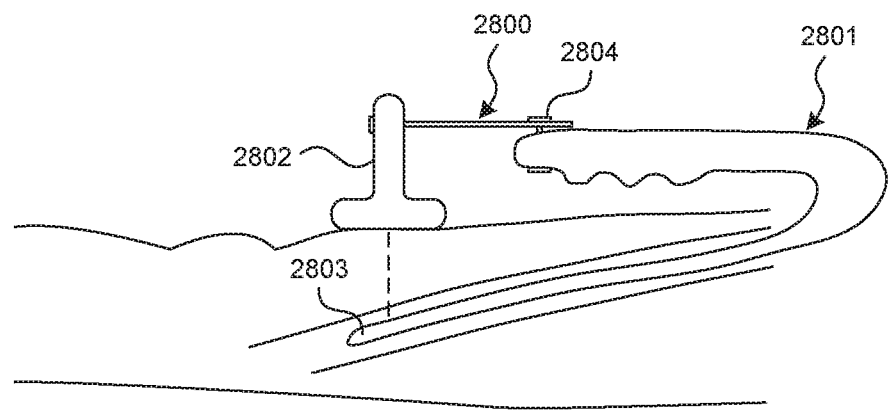
FIG. 28 illustrates an embodiment of a coupling mechanism to attach an ultrasound probe onto the handle of a device for accessing a valve creation site.

FIG. 28 depicts a coupling mechanism 2800 on the handle 2801 of the device, to attach the ultrasound probe 2802, so that the probe 2802 may always be located at a useful longitudinal location with respect to the distal tip of the device 2803. As shown, a set pin configuration 2804 allows for small adjustments of this longitudinal location so that other planes along the length of the device can be seen.

Other Visualization Techniques

All embodiments described for other visualization techniques (covering FIG. 29, and all associated text that may or may not describe embodiments depicted in figures), can be used in combination with other components described for full valve creation, including but not limited to: locating a valve creation site, creating wall apposition, hydrodissection, gaining access into an intra-mural space, use of other visualization methods, creation of an intra-mural pocket, valve mouth opening, and valve fixation. An example of one way in which to combine these embodiments to complete the valve creation procedure is depicted in FIG. 19. The embodiments depicted here can be used in combination with these or similar techniques to create a full valve geometry. Another similar example of one way in which to combine embodiments to complete the valve creation procedure is depicted in FIG. 30. The embodiments depicted here can be used in combination with these or similar techniques to create a full valve geometry.

Alternate embodiments include use of intravascular ultrasound (IVUS) for determination of potential valve creation sites, vein access and advancement to the valve creation site, the valve creation procedure, and for confirmation of success following the procedure.

Other embodiments utilize contrast fluoroscopy for determination of potential valve creation sites, vein access and advancement to the valve creation site, the valve creation procedure, and for confirmation of success following the procedure.

Figure 29:
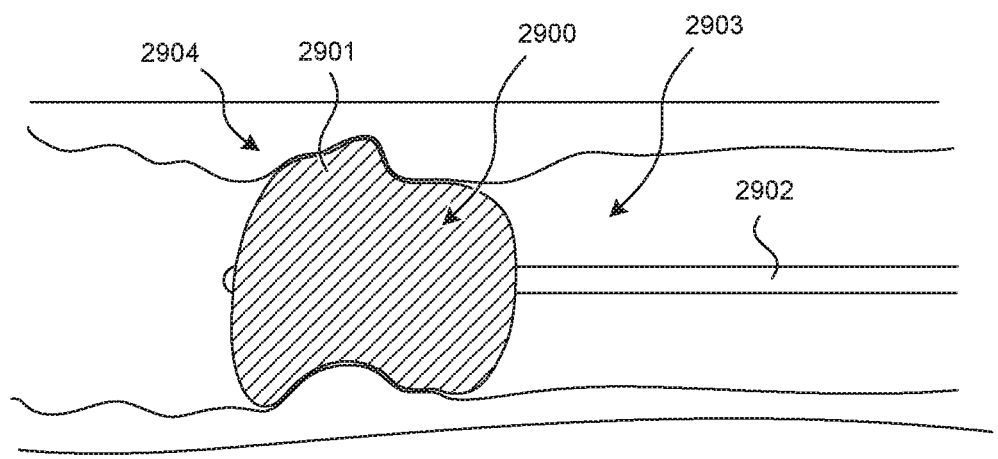
FIG. 29 illustrates an embodiment of a device for determining potential valve creation sites that includes a compliant balloon that can be filled with a contrast medium or covered with a piezoelectric array circuit.
Figure 30A:
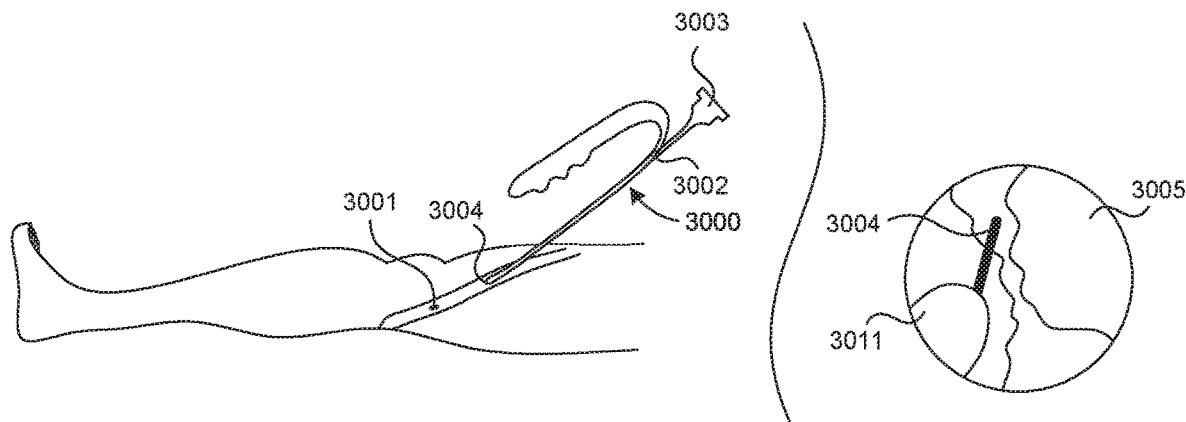
FIGS. 30A-30G illustrate an embodiment of a method for valve creation which uses a variety of the devices described herein.
Figure 30B:
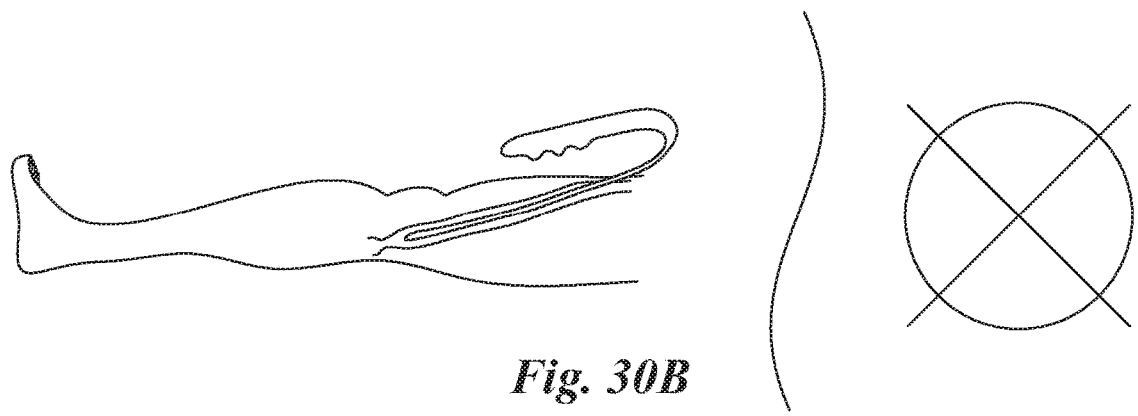
Figure 30C:
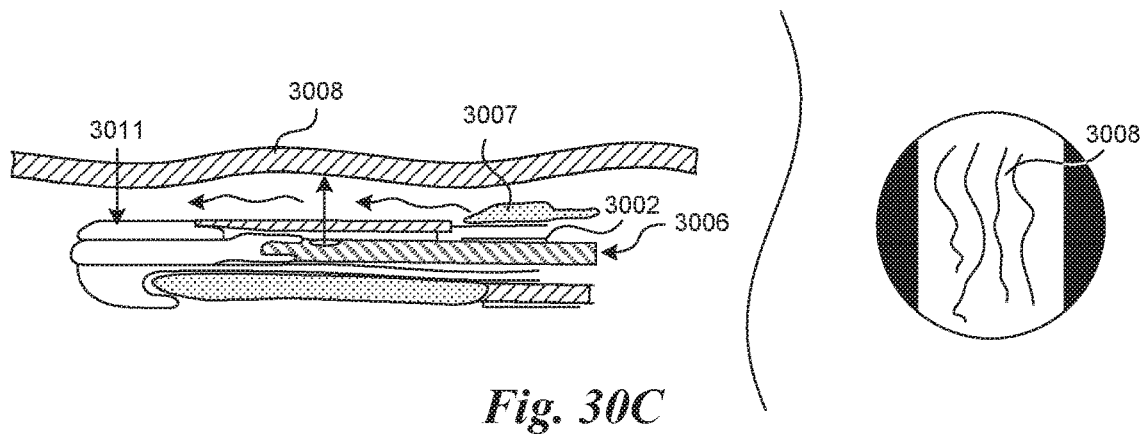
Figure 30D:
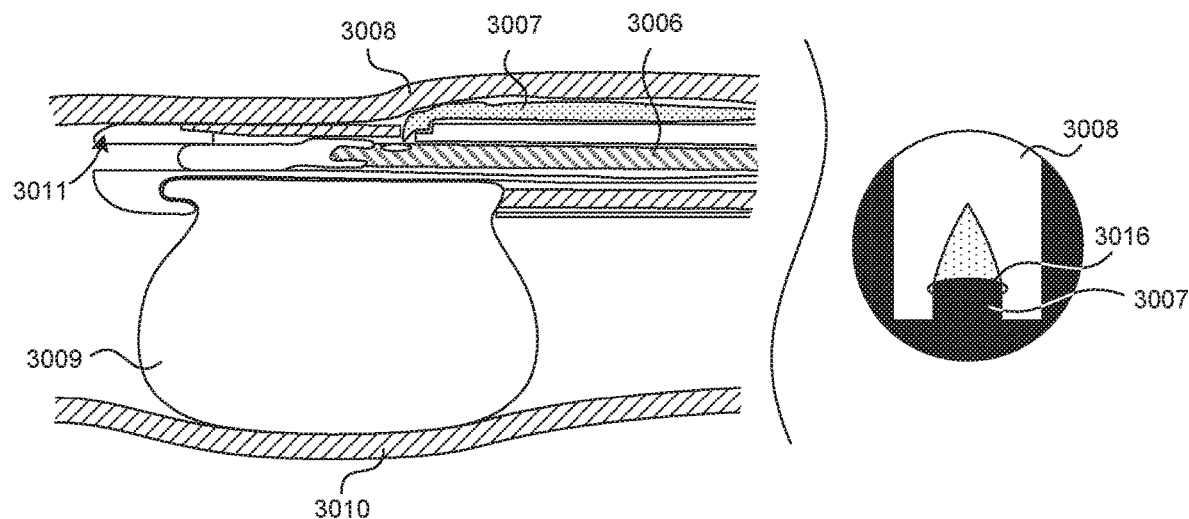
Figure 30E:
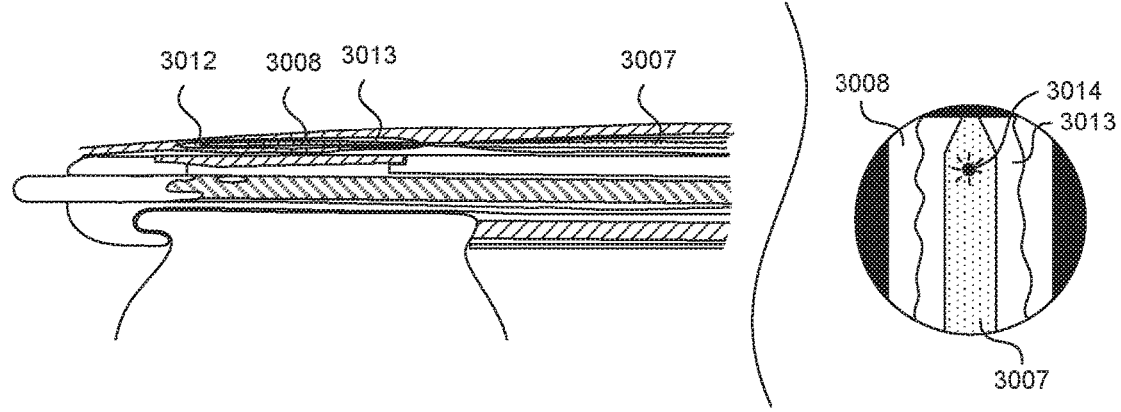
Figure 30F:
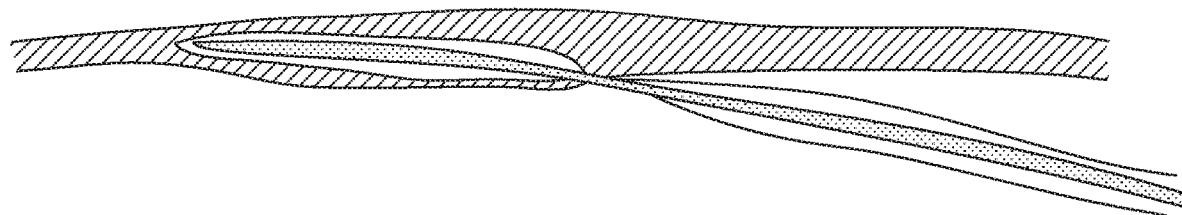
Figure 30G:
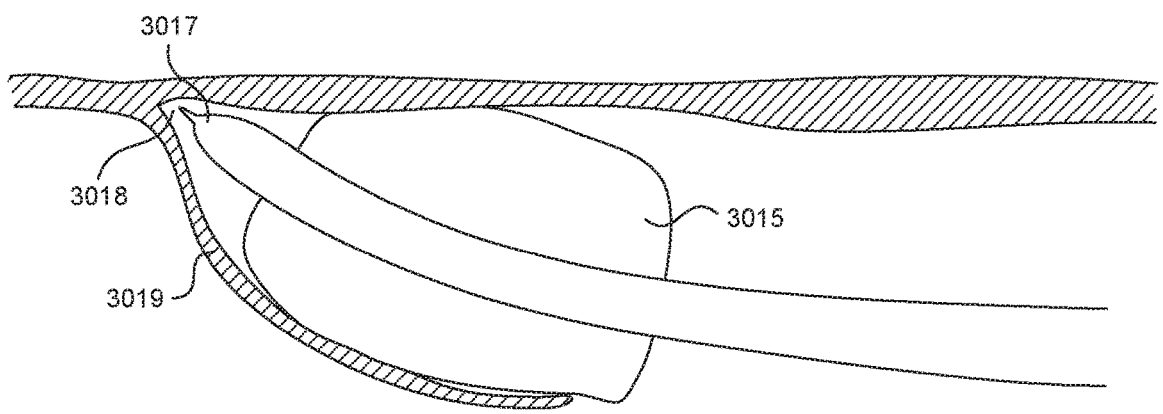

One specific embodiment for determination of potential valve creation site can be used in conjunction with contrast fluoroscopy, external or intravascular ultrasound, or direct visualization. FIG. 29 depicts the use of an ultra-compliant balloon 2900 filled with a contrast medium 2901 if necessary for the given visualization technique. This balloon 2900 is attached to a support tube 2902 with an inflation lumen. The support tube 2902 is advanced to a vessel segment 2903 of interest and the balloon 2900 is inflated to a certain pressure, which corresponds to a certain apposition on the vessel wall 2904. Due to its compliant nature, the balloon will conform to the abnormalities on the vessel wall 2904 rather than flatten out these abnormalities. In this way, the profile of the balloon can be used to assess the relative smoothness or roughness of a vein wall segment. This profile can be assessed by any of the aforementioned techniques to determine if a location in a vessel is an appropriate valve creation site.

An alternate embodiment of this ultra-compliant balloon is to utilize a piezoelectric array circuit along the surface of the balloon, which allows for measurement of surface abnormalities on the balloon (which correspond to surface abnormalities on the vessel wall), because deformities in the balloon surface (and thus the circuit) cause changes in resistance in the circuit. Other non-mentioned methods for determining the shape of such a balloon can be employed to make this surface smoothness determination.

Monocuspid Valve Creation Device and Method

FIG. 30 depicts a complete method for valve creation, which utilizes many, but not necessarily all, of the individual embodiments described in this and other related applications. The circular aspect of the figures to the right are depictions of the direct visualization that might be experienced during that point in the procedure. FIG. 30A depicts insertion of a rigid tubular structure 3000 into the vessel 3001. An open-ended visualization lumen 3002 and a direct visualization mechanism 3003 are incorporated into this embodiment, as well as a valve navigating antennae 3004. This configuration is utilized to advance the rigid device 3000 through the vasculature. A saline burst (not depicted) is utilized through the visualization lumen periodically to help with visualization of the surrounding wall and valves 3005. Using this visualization a potentially suitable vessel section is chosen for further investigations (due to absence of side branches and some evidence of a smooth wall). As depicted in FIG. 30B, the forward facing visualization mechanism 3003 is removed. FIG. 30C depicts a angled visualization mechanism 3006 that has been introduced into the visualization lumen 3002. Using periodic saline burst through the pre-loaded puncture element 3007, an image of the adjacent vascular wall 3008 can be viewed. The device is moved around and rotated subtly until a suitable patch of vascular wall is confirmed. As depicted in FIG. 30D, the expansion element, depicted here as a balloon 3009, is inflated to appose the opposite vessel wall 3010, which forces the distal end 3011 of the rigid tubular structure 3000 up against the vessel wall 3008 for valve creation. As depicted, the puncture element 3007 is advanced into the vessel wall 3008, which is conformed to the stepped surface of the rigid device 3000. This can be viewed under direct visualization as shown. As depicted in FIG. 30E, the puncture element 3007 is advanced within the vessel wall 3008, while expelling a hydrodissection fluid, here saline 3012, to create a sub-intimal space 3013 for the puncture element 3007 to enter. This can be viewed on direct visualization, and is aided by the puncture element identifier, shown here as a light 3014. FIG. 30F depicts the removal of the tubular structure 3000 (after deflation of the balloon 3009), and introduction of the valve creation balloon 3015 up to the puncture site 3016. The valve creation balloon 3015 with tapered tip 3017 is then introduced through the inlet 3016 and to the bottom of the intramural pocket 3018 (not depicted). FIG. 30G depicts inflation of the valve creation balloon 3015 to create a valve flap 3019. At this point a valve fixation mechanism is implemented to prevent the flap from re-adhering to the vessel wall. External ultrasound or direct visualization (by re-inserting the tubular structure) is used to confirm the valve functionality.

In a slightly different embodiment, the rigid tubular structure is not removed (as previously described) and direct visualization can be utilized through the valve creation procedure to confirm success of the procedure in real time.

All embodiments described in FIG. 30 can be used in combination with other components described for full valve creation, including valve securement. An example of one way in which to combine embodiments to complete the valve creation procedure is depicted in FIG. 19. The embodiments depicted here can be used in combination with these or similar techniques to create a full valve geometry.

Bicuspid Valve Creation Device and Method

The bicuspid valve creation device and method described in the following text and depicted in FIG. 31, can be used in combination with other components described for full valve creation, including but not limited to: locating a valve creation site, use of direct and/or indirect visualization methods, and valve fixation. An example of one way in which to combine these embodiments to complete the valve creation procedure is depicted in FIG. 19. The embodiments depicted here can be used in combination with these or similar techniques to create a full valve geometry. Another similar example of one way in which to combine embodiments to complete the valve creation procedure is depicted in FIG. 30. The embodiments depicted here can be used in combination with these or similar techniques to create a full valve geometry.

FIG. 31A depicts an embodiment of a bicuspid valve creation device and method. The embodiment includes two tool lumens 3100/3101 and two tool lumen exit ports 3102/3103, oriented about 180 degrees from each other as shown. The embodiment also includes an expansion element lumen 3104 in the middle. As shown in FIG. 31B, the embodiment also contains a flat, non-compliant balloon 3105, which expands outward through the two inflation windows 3106/3107, which are oriented about 180 degrees from each other. As shown the balloon 3105 is sufficiently flat such that when a vessel is stretched into a severe ellipse upon expansion, the taut vessel wall rests flat against the sides of the rigid tubular structure that house the tool lumen exit ports 3102/3103, such that when the puncture elements 3108/3109 are pushed out of the lumens 3102/3103, they contact the vessel wall at a consistent location at the same longitudinal location on the vessel wall. From here, the valve creation technique can be implemented twice, on both sides of the vessel wall. Then, a valve fixation technique can be utilized to affix the two valve flaps together, such as was described previously, to finish the procedure.

Side By Side Visualization and Associated Mechanisms and Functions

Scope Trough

FIGS. 32A-32G illustrate an embodiment of a visualization mechanism 3200 that can be incorporated in the distal portion of the elongate body of the devices described herein, such as a catheter for example. The distal end of the elongate body can have a guide or support structure 3202 having a partial cylinder or half pipe channel or trough 3204 with one open side positioned on a stiff flat section 3206 of the support structure 3202 surface of the catheter. The diameter of the trough 3204 can be slightly larger than the visualization tool in use: between 0.5 mm and 5 mm. In some embodiments, the diameter is between 1 mm and 3 mm. In some embodiments, the diameter is between 1.5 mm and 2 mm. In some embodiments, the trough depth is roughly half of the diameter of the trough.

Figure 32A:
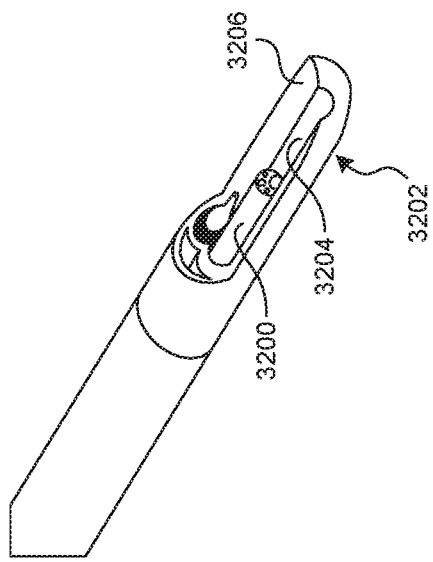
FIGS. 32A-32O illustrate an embodiment of a side by side visualization mechanism.
Figure 32B:
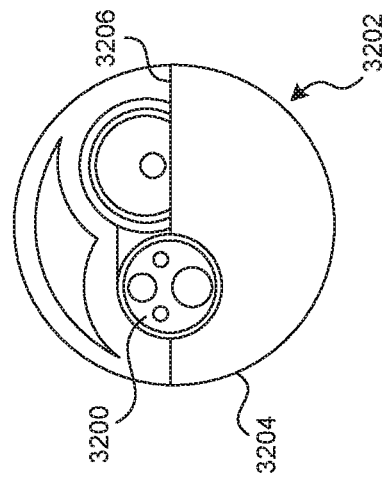
Figure 32C:
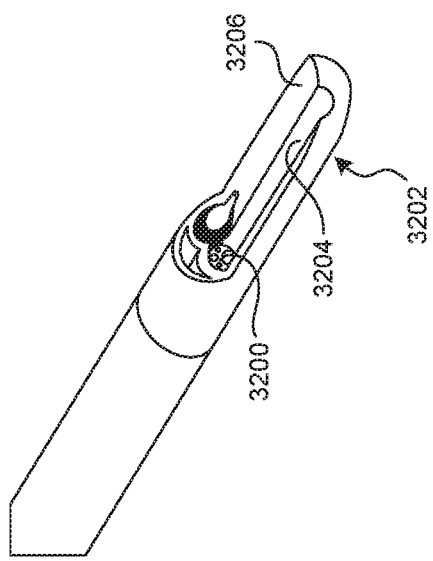
Figure 32D:
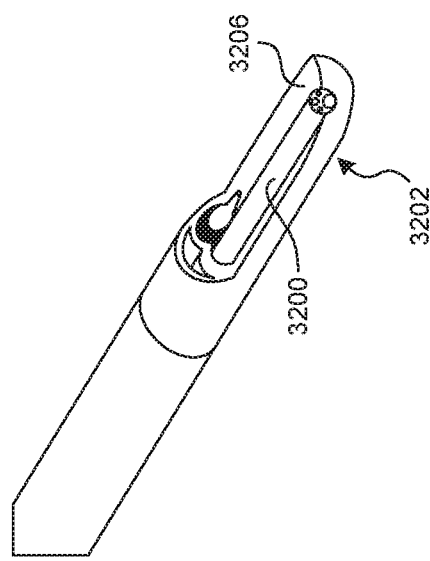
Figure 32E:
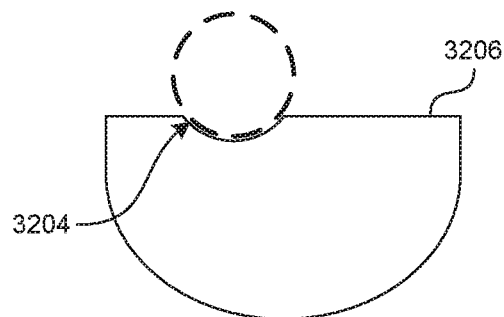
Figure 32F:
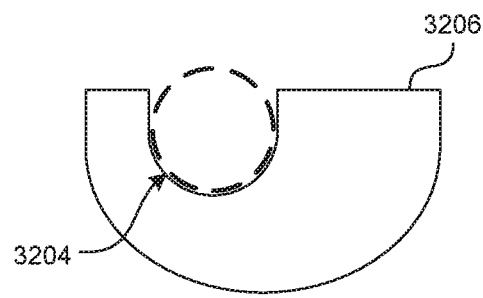

In other embodiments, the trough depth could vary between ¼ of the trough diameter as shown in FIG. 32E and ¾ of the trough diameter as shown in FIG. 32F.

As shown above, in some embodiments in which the trough depth is more than half of the trough diameter, the trough walls make up more than 180 degrees of an enclosure around the scope within (in some embodiments between about 180 and 270 degrees).

Figure 32G:
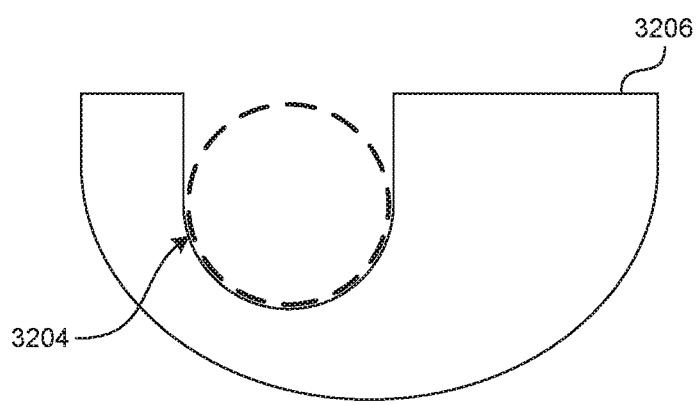

In some embodiments in which the trough depth is more than half of the trough diameter, the trough walls only curve 180 degrees, but can extend perpendicularly from the flat surface upwards from the two widest parts of the trough (half circular trough bottom with high walls), as shown in FIG. 32G.

Figure 32H:
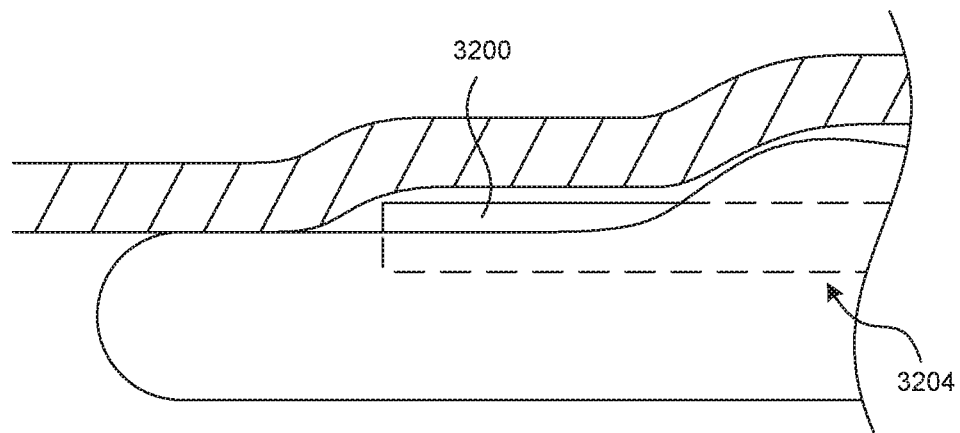

Scope Trough Function:

(1) The scope trough 3204 can function as a guiding mechanism to direct the advancement of a visualization mechanism 3200 in a straight line, as illustrated in FIG. 32H. This helps to minimize the amount of decisions the user must make, as it leaves on one degree of freedom, and is used for focused evaluation of a narrow strip of tissue for use as a valve structure.

Figure 32I:
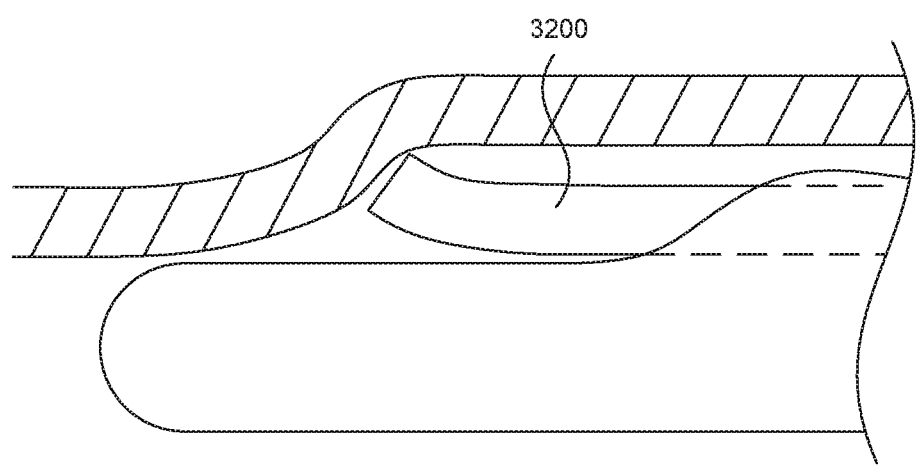

(2) Additionally, the trough 3204 provides a stand-off from the tissue, as illustrated in FIG. 32H. The trough 3204 hides the lower half of the front surface of the scope 3200 from the tissue, forcing the tissue to drape over the front surface of the scope 3200 at a shallower angle, thus preventing the scope face from directly (or perpendicularly) contacting the vessel wall or other anatomical structures. This prevents blurring or blockage of the visual field and bending of the scope 3200 upon further advancement following direct contact with tissue, which may happen when using a device without a trough, as illustrated in FIG. 32I.

Modes of Visualization:

The visualization mechanisms described herein can be used to assist with visualization via direct endoscopic visualization, catheter based ultrasound, catheter based OCT, catheter based MRI, or catheter based CT.

Lateral Viewing

Figure 32K:
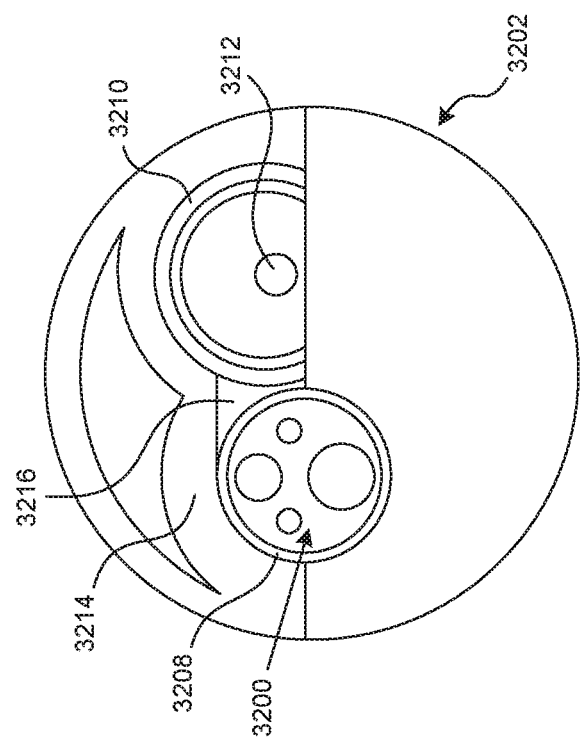
Figure 32J:
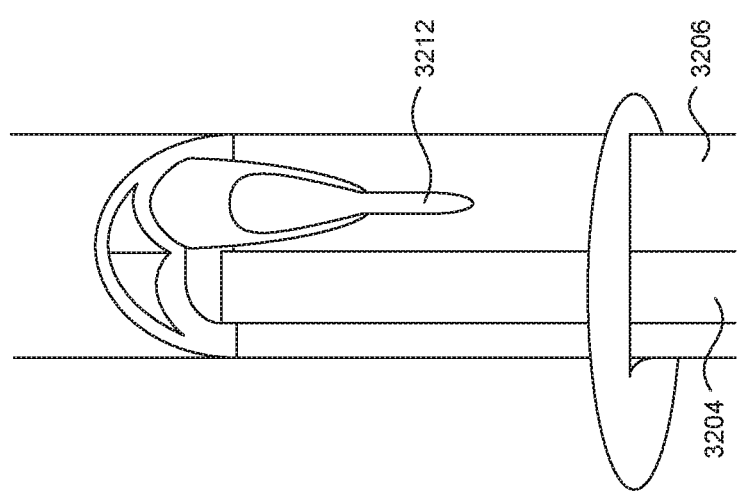

As illustrated in FIGS. 32J and 32K, a support structure 3202 near the distal end of a catheter can be constructed to support two parallel paths for a 1) visualization mechanism 3200 disposed in a visualization lumen 3208 and a 2) tool lumen 3210 (i.e., for vein wall puncture and valve creation using a puncture element and other tools 3212 described herein). These two functions run within substantially parallel support lumens 3208, 3210 through the length of the catheter and exit onto a substantially flat lateral surface 3206 of the catheter's distal end. The two lumens 3208, 3210 are positioned such that when the needle or puncture element 3212 is advanced out of the exit port and into the vessel wall, it can be seen laterally by an endoscope or other visualization mechanism 3200, as long as the scope has sufficiently wide angle of view. Lateral visualization requires the scope lumen 3208 and tool lumen 3210 to be very close together, with minimal distance between 0.00" and 0.01". In some embodiments, the distance between the scope lumen 3208 and tool lumen 3210 can be between 0.00" and 0.05".

Figure 32L:
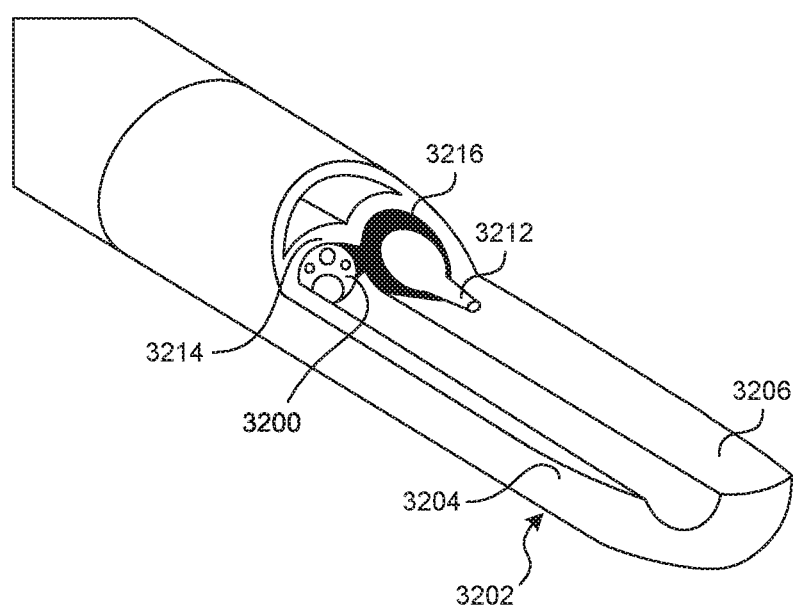
Figure 32M:
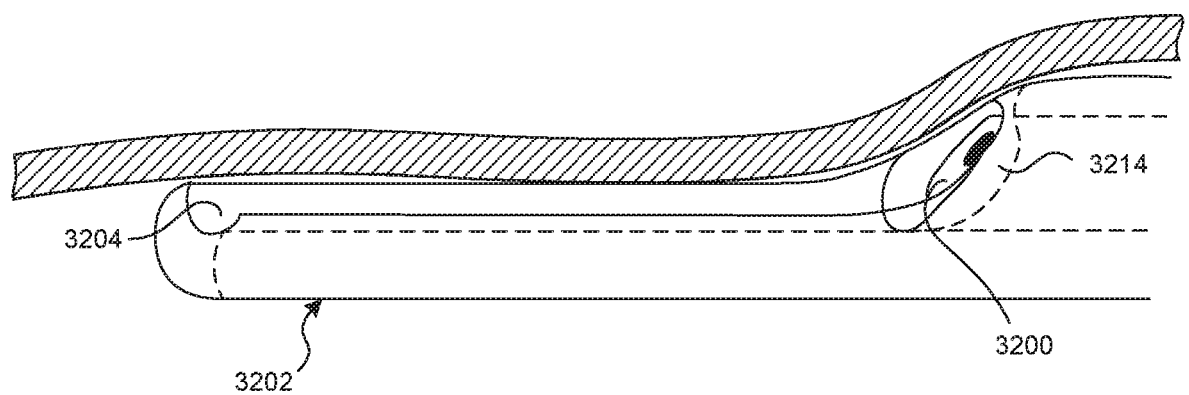

As illustrated in FIGS. 32K-M, an additional feature in this configuration is a protective viewing hood 3214 and a side-wall window 3216 between the two parallel lumens 3208, 3210. The protective viewing hood 3214 is configured out of a downward sloping termination of the lumen in which the scope 3200 is advanced to the exit port, and acts to shield the scope face from tissue before or after apposition balloon inflation. The side viewing window 3216 is developed by removal of the septum or wall which separates the scope lumen 3208 and the tool lumen 3210, so that the scope 3200 may see the tip of the puncture element 3212 laterally, while maintaining its proximal location within the scope hood 3214, even though the puncture element 3212 itself may be slightly forward from the tool lumen outlet. This window may be present for the distal 5-25 mm before the exit port.

Function of Lateral Visualization:

Use of side by side visualization includes, for example: evaluation of vessel wall prior to needle puncture, monitoring vessel wall puncture in real time, ruling out vessel reentry after vessel wall puncture and advancement (this is done by advancing the scope within the trough to check for needle re-entry), monitoring balloon insertion in real time, checking out balloon re-entry into lumen following advancement of balloon, monitoring balloon inflation in real time, and for evaluation of the created valve leaflet.

Efficient Flushing Lumens

Figure 32O:
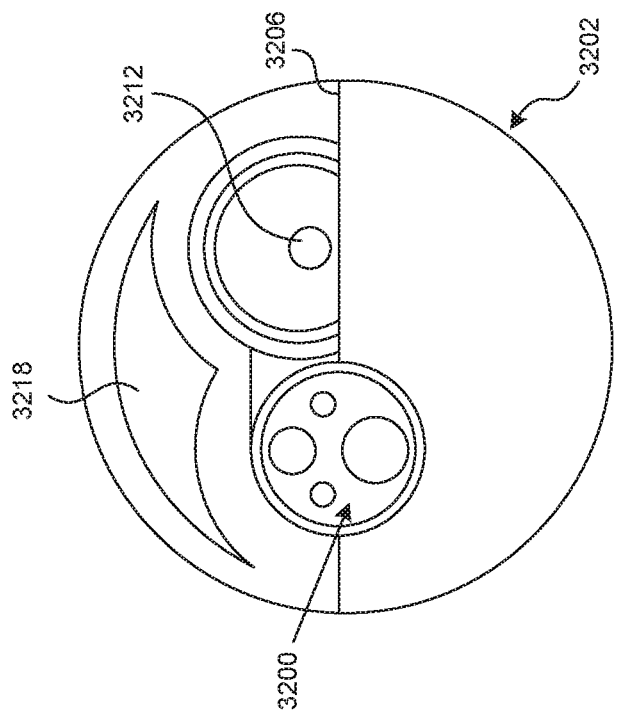
Figure 32N:
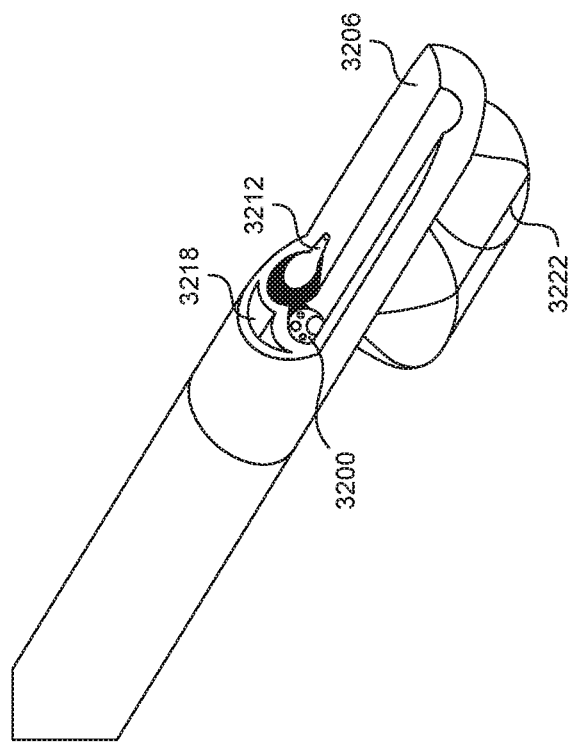

In order to monitor certain things with direct endoscopic visualization in a blood vessel, it is advantageous to have a mechanism to flush the visual field of blood. Embodiments of the present invention can include two flush lumens (above and below the scope lens) as illustrated in FIGS. 32N and 32O. In some embodiments as shown, the above flush lumen 3218 is stationary with respect to the mobile scope 3200, and takes a winged configuration to promote flow of saline or another flushing fluid out along the surface of the scope 3200 and tool 3212. The lower flush lumen 3220 can be part of the mobile scope 3200, and thus can be actuated with equal efficiency regardless of the scope location.

In other embodiments, the flush lumens 3218, 3220 may both be stationary to the device, or may both be mobile with the scope 3200. In some embodiments the flush lumen may be annular in shape so that it may surround the scope nearly or fully 360 degrees around.

In all embodiments with a flushing mechanism, a separate aid may be used in combination, as illustrated in FIG. 32N. Prior to flushing the visual field, an expansion mechanism 3222 (such as a semi-compliant balloon) can be expanded off the opposite side of the catheter as the scope 3200, thus forcing the scope side of the catheter into the vessel wall. In doing this, blood is evacuated from the space surrounding the scope 3200. The flushing mechanisms can still be used after expansion of the balloon 3222. It may be sufficient to leave a positive pressure drip bag connected to these lumens, such that blood is unable to enter into the cavity between the scope 3200 and the vessel wall, as the catheter will have or may have created a near seal against the wall, and the positive pressure from the flush lumens 3218, 3220 can prevent intrusion of additional blood following initial flushing.

Variations and modifications of the devices and methods disclosed herein will be readily apparent to persons skilled in the art. As such, it should be understood that the foregoing detailed description and the accompanying illustrations, are made for purposes of clarity and understanding, and are not intended to limit the scope of the invention, which is defined by the claims appended hereto. Any feature described in any one embodiment described herein can be combined with any other feature of any of the other embodiment whether preferred or not.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

What is claimed is:

1. A device for creating a dissection pocket in a human blood vessel, the device comprising:
    an elongated shaft having a first portion configured to be intravascularly positioned adjacent a dissection site and a second portion configured to be extracorporeally positioned;
    a trough extending distally in a longitudinal direction from the first portion of the elongated shaft, wherein the trough includes a bottom portion, sidewalls that extend from the bottom portion, and a tissue engaging portion along the sidewalls, wherein the tissue engaging portion comprises a substantially flat lateral surface configured to press against an opposing vessel wall;
    a first lumen extending through the shaft and terminating at a first port proximal to the trough;
    a second lumen extending through the shaft and terminating at a second port positioned between the sidewalls, wherein the second lumen is configured to receive an intravascular visualization device, and wherein the trough guides the visualization device in a longitudinal direction for evaluation of vessel tissue positioned proximate to the trough,
    wherein at least a portion of the tissue engaging portion is configured to define at least a portion of a periphery of the dissection pocket.

2. The device of claim 1 wherein at least a portion of the port is at an elevation corresponding to an elevation of a top portion of the tissue engaging portion.

3. The device of claim 1 wherein the port is positioned between the sidewalls.

4. The device of claim 1 wherein the sidewalls are curved.

5. The device of claim 1 wherein the device further includes an expandable member coupled to the first portion of the shaft.

6. The device of claim 1 wherein the device further includes an expandable member coupled to the first portion of the shaft and configured to be positioned circumferentially opposite the tissue engaging portion.

7. The device of claim 1 wherein at least a portion of the first port is at a first elevation and at least a portion of the second port is at a second elevation different than the first elevation.

8. The device of claim 1 wherein a top-most edge of the second port is at an elevation that is aligned with or below the tissue engaging portion of the trough.

9. The device of claim 1 wherein the trough has an open side exposed to the vessel and extending in a longitudinal direction along the sidewalls.

10. The device of claim 1, further comprising a puncture element configured to extend through the tool lumen and beyond the port, wherein, upon advancement beyond the port, the puncture element is configured to puncture the opposing vessel wall abutting the tissue engagement portion.

11. A device for creating a dissection pocket in a blood vessel, the device comprising:
    an elongated shaft having a first portion configured to be intravascularly positioned adjacent a dissection site and a second portion configured to be extracorporeally positioned;
    a trough extending distally in a longitudinal direction from the first portion of the elongated shaft, wherein the trough includes a bottom portion, sidewalls that extend from the bottom portion, and a tissue engaging portion along a longitudinal segment of the sidewalls;

a tool lumen extending through the shaft and terminating at a port proximal to the trough;

a visualization lumen extending through the elongated shaft and into the trough, wherein the visualization lumen and the trough are configured to allow a visualization device to visualize vessel tissue when the visualization device is in the trough, wherein at least a portion of the tissue engaging portion is configured to stretch the tissue in a plane at an elevation corresponding to an elevation of at least a portion of the port.

12. The device of claim 11 wherein:

the trough is open to the blood vessel along the longitudinal segment of the sidewalls; and the distal portion of the elongated shaft includes a recessed distal surface extending distally in a longitudinal direction from the first portion; and the sidewalls of the trough extend from the recessed distal surface toward the port.

13. The device of claim 11, further comprising a puncture element configured to extend through the tool lumen until the puncture element extends beyond the port.

14. A system for creating a dissection pocket in a blood vessel, the system comprising:

a tubular device comprising— an elongated shaft having a first portion configured to be intravascularly positioned adjacent a dissection site and a second portion configured to be extracorporeally positioned;

a trough extending distally in a longitudinal direction from the first portion of the elongated shaft, wherein the trough includes a bottom portion, sidewalls that extend from the bottom portion, and a tissue engaging portion along the sidewalls, and wherein the trough has an open side adjacent to a longitudinal segment of the tissue engagement portion and configured to be exposed to the blood vessel;

a tool lumen extending through the elongated shaft and terminating at an exit port proximal to the trough;

a visualization lumen extending through the elongated shaft and into the trough, wherein the visualization lumen is configured to receive a visualization device, and wherein— the trough is configured to allow for visualization of vessel tissue proximate to the tissue engagement portion when the visualization device is in the trough, and the trough is configured to guide the visualization device in a longitudinal direction.

15. The system of claim 14 wherein at least a portion of the exit port is positioned between the sidewalls and at an elevation aligned with an elevation of the tissue engagement portion.

16. The system of claim 14 wherein the tool lumen and the visualization lumen are spaced apart by a distance and extend along substantially parallel paths through the elongated shaft.

17. The system of claim 14, further comprising a puncture element configured to extend through the tool lumen and beyond the exit port, wherein, upon advancement beyond the exit port, the puncture element is configured to puncture a vessel wall opposing the tissue engagement portion.

* * * * *

UNITED STATES PATENT AND TRADEMARK OFFICE
CERTIFICATE OF CORRECTION

PATENT NO. : 10,758,335 B2  
APPLICATION NO. : 16/383504  
DATED : September 1, 2020  
INVENTOR(S) : Fletcher T. Wilson et al.

It is certified that error appears in the above-identified patent and that said Letters Patent is hereby corrected as shown below:

In the Specification

In Column 3, Line 46, delete "leaftlet." and insert -- leaflet. --, therefor.

In Column 3, Line 51, delete "leaftlet" and insert -- leaflet --, therefor.

In Column 5, Line 64, delete "FIG." and insert -- FIGS. --, therefor.

In Column 5, Line 66, delete "FIG." and insert -- FIGS. --, therefor.

In Column 6, Line 1, delete "FIG. 19A-19I" and insert -- FIGS. 19A-19I --, therefor.

In Column 6, Line 34, delete "32A-32O" and insert -- 32A-32O --, therefor.

In Column 8, Line 43, delete "saphenofemeral" and insert -- saphenofemoral --, therefor.

In Column 8, Line 65, delete "tubuilar" and insert -- tubular --, therefor.

In Column 13, Line 24, delete "15.58)" and insert -- 15.5B) --, therefor.

In Column 15, Line 13, delete "re-adherance." and insert -- re-adherence. --, therefor.

In Column 25, Line 25, delete "32O." and insert -- 32O. --, therefor.

Signed and Sealed this  
Second Day of February, 2021

Drew Hirshfeld  
*Performing the Functions and Duties of the*  
*Under Secretary of Commerce for Intellectual Property and*  
*Director of the United States Patent and Trademark Office*